United States Patent [19]
Martin, Jr. et al.

[11] Patent Number: 5,814,295
[45] Date of Patent: Sep. 29, 1998

[54] DETERMINATION OF LYMPH NODES ENRICHED IN TUMOR REACTIVE CELLS THEIR PROLIFERATION AND THEIR USE IN ADOPTIVE CELLULAR THERAPY

[75] Inventors: Edward W. Martin, Jr., Delaware, Ohio; Brian J. Czerniecki, Gaithersburg, Md.; Pierre L. Triozzi; Julian A. Kim, both of Columbus, Ohio

[73] Assignee: The Ohio State University Research Foundation, Columbus, Ohio

[21] Appl. No.: 271,902

[22] Filed: Jul. 13, 1994

Related U.S. Application Data

[63] Continuation-in-part of Ser. No. 93,088, Jul. 16, 1993, abandoned, which is a continuation-in-part of Ser. No. 866,839, Apr. 10, 1992, abandoned.

[51] Int. Cl.$^6$ .............................. A61K 51/00; G01N 1/00
[52] U.S. Cl. ...................... 424/1.49; 424/9.1; 424/9.322; 424/93.1; 424/93.7; 424/1.17; 424/1.41; 424/1.53; 424/1.57; 436/64; 435/7.24; 435/372; 435/372.2
[58] Field of Search ................................. 424/1.17, 1.41, 424/1.49, 1.53, 1.57, 1.69, 9.1, 9.322, 93.1, 93.7, 520, 529, 578, 577, 534, 93.71, 85.1, 85.2; 436/64; 128/654; 435/7.24, 29, 372, 372.1, 372.2, 372.3, 383–384, 386

[56] References Cited

U.S. PATENT DOCUMENTS

| | | | |
|---|---|---|---|
| 4,741,900 | 5/1988 | Alvarez et al. | 424/85 |
| 4,782,840 | 11/1988 | Martin, Jr. et al. | 128/654 |
| 5,041,289 | 8/1991 | Phillips et al. | 424/85 |
| 5,126,132 | 6/1992 | Rosenberg | 424/93 |

OTHER PUBLICATIONS

Morecki et al, Journal of Biological Response Modifiers, vol. 9 p. 463, 1990.
Yoshizawa et al, J. Immunol. vol. 147 p. 729, Jul. 1991.

*Primary Examiner*—Sheela Huff
*Attorney, Agent, or Firm*—Mueller and Smith, LPA

[57] ABSTRACT

The present invention is directed to a method for reliably determining lymph nodes enriched in tumor reactive cells, e.g., CD4+tumor-specific lymphocytes. This method includes the steps of administering to a patient an effective amount of a radiolabeled locator which specifically binds a marker produced by or associated with neoplastic tissue. Time is permitted to elapse following the administration for the radiolabeled locator to preferentially concentrate in any neoplastic tissue and for unbound radiolabeled locator to be cleared, so as to increase the ratio of photon emissions from neoplastic tissue to background photon emissions in the patient. After the time has elapsed, the patient is accessed with a radiation detection probe for determining lymph node sites exhibiting accretion of the radiolabeled locator by detecting with the probe elevated levels of radiation at the lymph node sites. The lymph node sites exhibiting such elevated levels of radiation are removed and subjected to gross visual analysis, though such sites alternatively may be subjected to histological analysis. Those determined and removed lymph nodes that also are determined to be tumor-free by gross observation or free of gross metastatic disease are selected and cultured to proliferate tumor reactive cells. The selected lymph nodes are subjected to mitogenic stimulation. The lymph nodes are cultured in the presence of Interleukin-2, anti-$CD_3$ monoclonal antibody, and neoplastic tissue which may be autologous or allogeneic tumor. The tumor reactive cells, proliferated can be used with adoptive immunotherapy regimens for mitigating the progression of tumor.

48 Claims, 6 Drawing Sheets

DETERMINATION OF LYMPH NODES ENRICHED IN TUMOR REACTIVE CELLS THEIR PROLIFERATION AND THEIR USE IN ADOPTIVE CELLULAR THERAPY

CROSS-REFERENCE TO RELATED APPlICATIONS

This application is a continuation-in-part of application Ser. No. 08/093,088, filed Jul. 16, 1993 (now abandoned), which is a continuation-in-part of application Ser. No. 07/866,839, filed Apr. 10, 1992 (now abandoned), the disclosures of which are expressly incorporated herein by reference.

BACKGROUND OF THE INVENTION

The following abbreviations will be used herein:

| | |
|---|---|
| LNL | Lymph node lymphocyte(s) |
| PBL | Peripheral blood lymphocyte(s) |
| TIL | Tumor-infiltrating lymphocyte(s) |
| LAK | Lymphokine-activated killer |
| IL-2 | Interleukin-2 |
| Anti-CD$_3$ | Anti-CD$_3$ monoclonal antibody |
| CC49 | CC49 monoclonal antibody |
| TAG | Tumor-associated glycoprotein |
| Auto | Autologous |
| Allo | Allogeneic |
| Glio | Human glioma cultured cell line |
| CAR1 | Human carcinoid tumor |
| CEA | Carcinoembryonic antigen |
| MoAB | Monoclonal antibody |
| BSM | Bovine submaxillary mucus |
| PBMC | Peripheral blood mononuclear cells |
| WD124 | Cultured human colon carcinoma cell line |

Approximately 50 percent of patients diagnosed with colorectal cancer will develop metastatic disease outside the colon or rectum. The majority of these patients will not be curable by second-look surgery, because the disease will be intrahepatic as well as extrahepatic. Additional therapies are needed to improve survival of patients with this disease.

Adoptive immunotherapy provides an attractive treatment modality for cancer therapy. Using lymphokines such as Interleukin-2 (IL-2) and lymphokine-activated killer cells (LAK) derived from patient peripheral blood, Rosenberg, et al. demonstrated that a small but significant percentage of patients with melanoma and renal cell cancer achieve a long-lasting response. Rosenberg, et al., "Adoptive Cellular Therapy: Clinical Applications", *Biologic Therapy of Cancer*, DeVita, et al. (Eds.), J. B. Lippincott Company, Philadelphia, Pa., 1991. A second approach to adoptive immunotherapy has been to expand lymphocytes from tumors in culture. Rosenberg, "Adoptive Cellular Therapy: Clinical Applications", *Biologic Therapy of Cancer*, DeVita, et al. (Eds), J. B. Lippincott Company, Philadelphia, Pa., p. 241 (1991); Topalian, et al. "Tumor Infiltrating Lymphocytes: Evidence of Specific Immune Reactions Against Growing Cancers in Mice and Human", *Important Advances in Oncology* 1990, DeVita, et al. (Eds), J. B. Lippincott Company, Philadelphia, Pa., p. 19 (1990), and Rosenberg, et al., "Use of Tumor-Infiltrating Lymphocytes and Interleukin-2 in the Immunotherapy of Patients with Metastatic Melanoma", *N. Engl. J. Med.*, 25:1671, 1988. Using these tumor-infiltrating lymphocytes (TIL), several research groups have documented superior tumor cytolytic activity and better trafficking of these TIL cells to tumor than LAK cells. Rosenberg, et al., *N. Engl. J. Med.*, id.; Dillman, et al., "Continuous Interleukin-2 and Tumor-Infiltrating Lymphocytes as Treatment of Advanced Melanoma", *Cancer*, 68:1, 1991; Kradin, et al., "Tumor-Infiltrating Lymphocytes in Interleukin-2 in Treatment of Advanced Cancer", *Lancet*, 33:577, 1989; and Bukowski, et al., "Clinical Results and Characterization of Tumor-Infiltrating Lymphocytes with or without Recombinant Interleukin-2 in Human Metastatic Renal Cell Carcinoma", *Cancer Res.* 51:4199, 1991. Overall, these TIL cells appear to be therapeutically effective for patients with melanoma. Tumor-infiltrating lymphocytes have been generated from many solid tumors, including colon and breast cancer; however, these cells do not appear to mediate tumor-specific cytolytic activity in vitro and it remains to be determined if these cells will be effective in adoptive immunotherapy models. Rosenberg, "Gene Therapy of Cancer", *Important Advances in Oncology*, 1992, DeVita, et al. (Eds), J. B. Lippincott Co., New York, N.Y., pp 17–18, 1992.

Another exciting approach to tumor therapy with tumor-specific lymphocytes is the placement of cytokine genes in the cells which can deliver cytokines locally to the tumor. Kasid, et al., "Human Gene Transfer: Characterization of Human Tumor Infiltrating Lymphocytes as Vehicles for Retroviral-Mediated Gene Transfer in Man", *Proc. Natl. Acad. Sci. USA*, 87:473–477, 1990; and Rosenberg, et al., "Gene Transfer into Humans: Immunotherapy of Patients with Advanced Melanoma Using Tumor Infiltrating Lymphocytes Modified by Retroviral Gene Transduction", *New Engl. J. Med.*, 323:570–578, 1990. It has been shown in several model systems that tumor cells transfected with various cytokine genes including IL-2, gamma interferon, and tumor necrosis factor (TNF), are more immunogenic and less tumorigenic than parent cells that do not produce cytokines. Gansbacher, et al., "Retroviral Vector-Mediated Gamma Interferon Gene Transfer into Tumor Cells Generates Potent and Long Lasting Antitumor Immunity", *Cancer Res.* 50: 7820–7825, 1990; Gansbacher, et al., "Interleukin 2 Gene Transfer into Tumor Cells Abrogates Tumorigenecity and Induces Protective Immunity", *J. Exp. Med.*, 172:1217–1224, 1990; and Blankenstein, et al., "Tumor Suppression after Tumor Cell-Targeted Tumor Necrosis Factor-Alpha Gene Transfer", *J. Exp. Med.* 173:1047–1052, 1991. This would suggest that local production of cytokines near tumor cells impacts favorably by inhibiting tumor growth and stimulating an immune response. Indeed, it would be useful to find lymphocytes that recognize tumor and are capable of secreting various cytokines in response to tumor and to use these cells for adoptive immunotherapy. Recently, it has been shown that certain TIL cells that secrete gamma-interferon and TNF-alpha mediate tumor regression in vivo, even though they do not display direct tumor cytotoxicity in vitro. Barth, et al., "Interferon-Gamma and Tumor Necrosis Factor Have a Role in Tumor Regression Mediated by Murine CD$_8$+ Tumor-Infiltrating Lymphocytes", *J. Exp. Med.*, 173:647, 1991.

Several problems—including the difficulty of obtaining TIL cells from most solid tumors such as breast and colorectal cancer, the type of lymphocytes which expand under these conditions, and the long periods of culture time needed to generate TIL cells—have made widespread application to most tumors prohibitive. An alternative source of tumor lymphocytes may be lymph nodes. Several laboratories have demonstrated a tumor-specific immune response in regional lymph nodes from cancer patients, including breast, head and neck, pancreas, and colon. Hoover, et al., "Activation and In Vitro Expansion of Tumor-Reactive T Lymphocytes from Lymph Nodes Draining Human Primary Breast Cancers", *J. Surg. Oncol.*, 46:117, 1991; Cozzolino, et al., "Characterization of Cells from Invaded Lymph Nodes in Patients with Solid Tumors, Lymphokine Requirement for Tumor-Specific Lymphoproliferative Response", *J. Exp. Med.*, 166:303, 1987; Barnd, et al., "Specific, Major Histocompatibility Complex-Unrestricted Recognition of Tumor-Associated Mucins by Human Cytotoxic T-cells", *Proc. Nat. Acad. Sci. USA*, 86:7159–7163, 1989; and Vose, et al., "Tumor Reacting Lymphocytes Stimulated in Mixed Lymphocyte and Tumor Culture", *Cancer Immunol. and Immunother.*, 15:227–236 (1983). In experimental animal models, regional lymph nodes have been shown to contain tumorspecific pre-effector cells which, when expanded in vitro, can eliminate experimental metastases. Yoshizawa, et al., "Activation by Anti-CD$_3$ of Tumor-Draining Lymph Node Cells for Specific Adoptive Immunotherapy", *Cell Immunol.*, 134:473, 1991; and Yoshizawa, et al., "Specific Adoptive Immunotherapy Mediated by Tumor-Draining Lymph Node Cells Sequentially Activated by Anti-CD$_3$ and IL-2", *J. Immunol.*, 147:729, 1991. In animal models, the timing of lymph node removal and the size of primary tumor are critical factors in the ability to detect pre-effector lymphocytes. Yoshizawa, et al., "Activation by Anti-CD$_3$ of Tumor-Draining Lymph Node Cells for Specific Adoptive Immunotherapy, supra; and Sakai, et al., "Phenotype Analysis in Cellular Mechanisms of Pre-Effector T-Lymphocyte Response to a Progressive Syngeneic Murine Sarcoma", *Cancer Res.*, 50:4371–4376, 1990. These lymphocytes also can be expanded in vitro in the absence of tumor stimulation by using anti-CD$_3$ and IL-2. If identified in humans, pre-effector lymphocytes potentially could be valuable cells for adoptive immunotherapy. In humans, it is difficult to select reliable nodes which contain a tumor-specific immune response, therefore limiting the ability to use lymph node lymphocytes (LNL) as a source of tumor-specific adoptive immunotherapy.

The disclosures of the foregoing references are expressly incorporated herein by reference

BROAD STATEMENT OF THE INVENTION

Broadly, the present invention in one aspect is directed to a method for reliably determining lymph nodes enriched in tumor reactive cells, e.g., CD4+ tumor-specific lymphocytes, often called T-helper cells or T-helper lymphocytes. This method comprises the steps of administering to a patient an effective amount of a radiolabeled locator which specifically binds a marker produced by or associated with neoplastic tissue, e.g. cancer. Time then is permitted to elapse following the administration for the radiolabeled locator to preferentially concentrate in any neoplastic tissue and for unbound radiolabeled locator to be cleared, so as to increase the ratio of photon emissions from neoplastic tissue to background photon emissions in the patient. After the time has elapsed, the patient is accessed (e.g. preferably, surgically; note: use of a laproscope may be impractical, though use of such instruments is not precluded in the present invention) with a radiation detection probe for determining lymph node sites exhibiting accretion of the radiolabeled locator by detecting with the probe elevated levels of radiation at the lymph node sites. The lymph node sites exhibiting such elevated levels of radiation then are removed and subjected to gross visual analysis, though such sites alternatively/additionally may be subjected to histological analysis, e.g. hematoxylin and eosin (H&E) histologic evaluation.

Those determined and removed lymph nodes that also are determined to be tumor-free by gross observation or free of gross metastatic disease (i.e., those lymph nodes that visually appear normal, but which take-up antibody) then are selected and cultured to proliferate tumor reactive cells, e.g., tumor-specific T lymphocytes therein. When such node sites have been subjected to histological analysis, those that are determined by H&E to be histologically negative are selected for expansion. The selected lymph nodes then are subjected to mitogenic stimulation. Advantageously, then, the lymph nodes are cultured in the presence of, for example, Interleukin-2 (IL-2), anti-CD$_3$ monoclonal antibody, and, optionally, neoplastic tissue which may be autologous or allogeneic tumor. The tumor reactive cells, e.g., T lymphocytes, proliferated then can be used in accordance with adoptive immunotherapy regimens for mitigating (moderating) the progression of tumor. The expanded or proliferated tumor reactive cells, e.g., T lymphocytes, are an effective therapeutic agent in the treatment of cancer.

Presently, CD4+ tumor-specific lymphocytes are believed to be involved in the therapeutic effect displayed by the inventive therapeutic agent, though this has not been proven. The lymph nodes removed certainly can be characterized by their CD4+ tumor-specific lymphocyte content, however, whether or not such lymphocytes are significant in mitigating tumor progression. "Tumor reactive cells" was the term chosen to describe the active cells (active in mitigating the progression of tumor) contained in the expanded removed lymph nodes. While such "active cells" are believed to comprise CD4+ tumor-specific lymphocytes, this is not a limitation of the present invention.

Advantages of the present invention include the ability to select with certainty lymph nodes reliably enriched in tumor reactive cells, e.g., CD4 tumor-specific lymphocytes. An additional advantage is the ability to remove diseased tissue from the patient by the lymph node removal. Another advantage of the present invention is the ability to expand tumor reactive cells including T lymphocytes readily for forming a therapeutic agent for in vivo mitigation of tumor progression. These and other advantages will be readily apparent to those skilled in the art based upon the disclosure contained herein.

Figure 1:
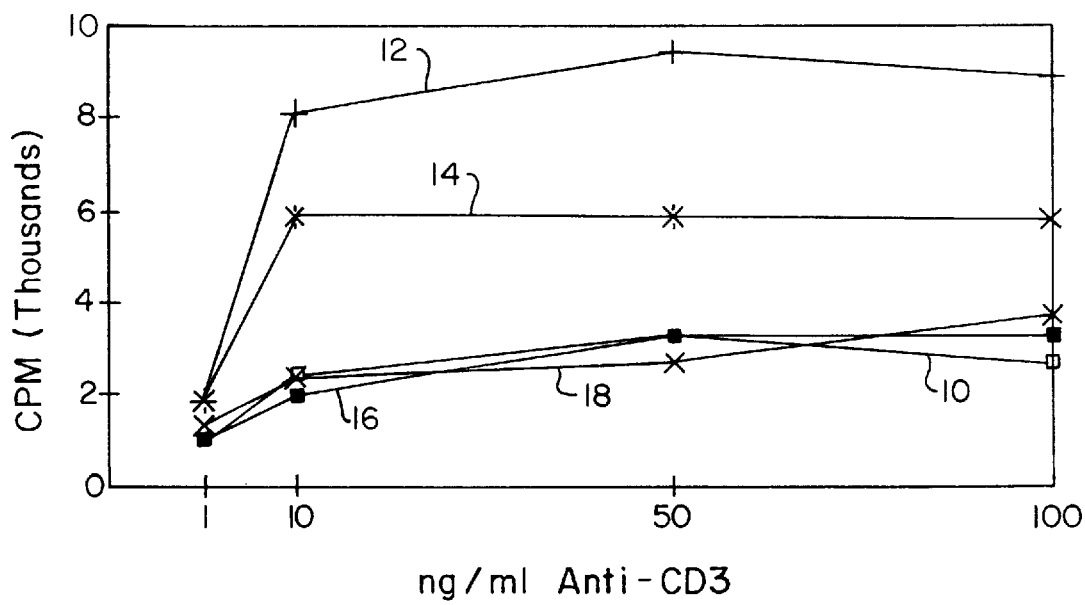
FIG. 1 graphically displays Type I LNL proliferation in a mixed tumor lymphocyte culture with autologous (irradiated) tumor in the presence of IL-2 and various concentrations of anti-CD$_3$ as measured by [$^3$H] thymidine incorporation. This same data is displayed in Table 2. LNL ($10^4$ cells) were cultured with autologous (Auto) or allogeneic (Allo) colon cancer cells isolated from fresh tumor, or with autologous or allogeneic PBL ($5\times10^3$ cells, irradiated 4000 rads) in 96 well plates. Four days later [$^3$H] thymidine (1 uCi/well) was added and 18 hours later the plates were harvested and thymidine incorporation determined by liquid scintillation counting. All cultures contained 20 $\mu$g/ml IL-2. Incubation of LNL alone with tumor, tumor cells with growth factors alone, or LNL alone resulted in no proliferation.

The experimental results reported in the drawings will be discussed in detail below.

DETAILED DESCRIPTION OF THE INVENTION

Until recently, the in vivo selection of diseased (e.g., tumor bearing) lymph nodes was limited to the surgeon's visual selection and the pathologist's diagnosis. Nieroda, et al, "Radioimmunoguided Surgery (RIGS) in Recurrent Colorectal Cancer", Cancer Detection and Prevention, Vol. 14, Issue 6, pages 651–656 (1990), and "Radioimmunoguided Surgery in Primary Colon Cancer", Cancer Detection and Prevention, Vol. 15, Issue 3, pages 225–229 (1991) disclose a method for staging of patients afflicted with neoplastic tissue by the Radioimmunoguided Surgery™ system using a Neoprobe® RIGS® gamma detecting probe (Radioimmunoguided Surgery™ is a trademark, and Neoprobe® and RIGS® are registered trademarks, of Neoprobe Corporation, Columbus, Ohio). Lymph node involvement as determined by such system enables the surgeon and/or oncologist to appropriately stage the patient, e.g., upstage the patient for adjuvant chemotherapy.

Such staging development is based on U.S. Pat. No. 4,782,840 (the disclosure of which is expressly incorporated herein by reference) which discloses a much improved method for locating, differentiating, and removing neoplasms. Such technique utilizes a radiolabeled antibody and a portable radiation detection probe which the surgeon can use intraoperatively in order to detect sites of increased radioactivity. Such procedure is known as the RIGS® system and is successful because of the recognition that tumor detection should be delayed until the blood pool background of circulating radiolabeled antibody has had an opportunity to be cleared from the body so as to enhance the photon emissions or radiation emitted by the tumors compared to surrounding tissue. Fortuitously, the '840 patent discloses the ability of the radiolabeled antibody to remain bound to or associated with neoplastic tissue for extended periods of time with the radio tag still bound thereto. Moreover, even though the accretion of radioactivity at the tumor site decreases over time, the blood pool background and surrounding tissue (relative to the tumor sites) decrease at a much greater rate so that the radioactive sites can be determined readily utilizing a hand-held probe, such as a Neoprobe® RIGS® 1000 radiation detector.

Using the RIGS® system of the '840 patent with the Neoprobe® RIGS® 1000 radiation detector and $^{125}$I CC49 monoclonal antibody, lymph nodes have been identified and originally placed into five classes. Later work revealed that such an extensive classification was not necessary in order to select appropriate lymph nodes for expansion and formation into a therapeutic agent for the mitigation of tumor progression. While some of the following discussion refers to such original lymph node classification, it should be understood that use of such a classification system is not necessary to practice of the present invention. The early classification system developed is set forth in Table 1 below.

TABLE 1

| Lymph Node Classes | |
| --- | --- |
| Type 0 | RIGS ® Probe (−), Histology (−) |
| Type I | RIGS ® Probe (+), Histology (−) |
| Type II | RIGS ® Probe (+), Occult Tumor Present |

TABLE 1-continued

Lymph Node Classes

| | |
|---|---|
| Type III | RIGS ® Probe (+), Routine Histology (+) (Macroscopic) |
| Type IV | RIGS ® Probe (−), Routine Histology) (+) (Macroscopic) |

Type 0 lymph nodes have no detectable radiation activity and no histologic evidence of tumor. Type I nodes are radioactively positive, but negative by routine H&E histology;. Type II nodes are radioactively positive and contain evidence of occult tumor. Type III nodes are radioactively positive and contain histologic evidence of tumor. Type IV nodes are radiation negative but contain evidence of tumor.

Anatomically, the majority of Type I nodes are found in the periportal lymph nodes, celiac lymph nodes, and the suprapancreatic aortic lymph nodes. In patients with primary colorectal cancer, about 30% of the draining regional colonic mesenteric nodes are Type I. Type III and Type IV nodes for the most part are found in the colonic mesentery near the tumor. When Type I lymph nodes are analyzed further by serial sectioning or by cytokeratin antibodies, about 40% of Type I nodes have evidence of tumor, making them actually Type II lymph nodes. For purposes of the present invention, Type I nodes are determined by H&E histology and those lymph nodes are selected for culturing to proliferate the tumor reactive cells, e.g., CD4+ T lymphocytes. Preferably, however, the apparent Type I lymph nodes are subjected to serial sectioning or cytokeratin antibodies for retyping those lymph nodes that are positive by histology and, thus, contain occult tumor, making such lymph nodes actually fall into Type II. Thus, LNL with little or no tumor are used for culturing to proliferate CD4+ tumor-specific lymphocytes. Further discussion concerning lymph node classes can be found in Arnold, et al., "Radio-immunoguided Surgery Challenges Traditional Decision Making in Patients with Primary Colorectal Cancer", *Surgery*, Vol. 112, No. 4, pp 624–630 (October 1992); and Arnold, et al., "Intraoperative Detection of Colorectal Cancer with Radioimmunoguided Surgery and CC49, a Second-Generation Monoclonal Antibody", *Annals of Surgery*, Nol. 216, No. 6, 627–632 (December 1992), the disclosures of which are expressly incorporated herein by reference.

The first step of the method of the present invention comprises the administration to the patient of an effective amount of a radiolabeled locator which specifically binds a marker produced by or associated with neoplastic tissue. As stated above, a "locator" includes a substance which preferentially concentrates at the tumor sites by binding with a marker (the cancer cell or a product of the cancer cell, for example) produced by or associated with neoplastic tissue or neoplasms. Appropriate locators today primarily include antibodies (whole and monoclonal), antibody fragments, chimeric versions of whole antibodies and antibody fragments, and humanized versions thereof. It will be appreciated, however, that single chain antibodies (SCAs, such as disclosed in U.S. Pat. No. 4,946,778) and like substances have been developed and may similarly prove efficacious. Biochemistry and genetic engineering may yet produce substances which mimic the function of antibodies in selectively concentrating at the sites of neoplastic tissue (perhaps, even hormones, peptides and other proteins, or the like), though such substances may not be subsumed within the traditional definition of "antibody". "Locator" was chosen as the term to include present-day antibodies and equivalents thereof, as well as those substances yet to be determined which mimic antibodies in the inventive method disclosed herein.

Presently, antibodies useful in the present invention include anti-TAG antibodies, such as for example, B72.3 (an anti-TAG 72 antibody, Dr. Jeffrey Schlom, National Cancer Institute), CC49 (a second generation B72.3 antibody, see Arnold, et al., "Intraoperative Detection of Colorectal Cancer with Radioimmunoguided Surgery™ (RIGS®) and CC49 a Second-Generation Monoclonal Antibody (Mab)" *Ann. Surg.*, accepted for publication, *Cancer Res.* 50, 6987–6994, Nov. 1, 1990; *Cancer Res.* 48, 4597–4603, Aug. 15, 1987; *J. Clin. Lab. Analysis* 3: 369–369 (1989); *Biol. Chem*, Hoppe-Seyler, 1989, 370:21–26; *Cancer Res.* 50: 4885–4890, Aug. 15, 1990; *Cancer Res.*, 48: 4588–4596, 1988; *Cancer Res.*, 50: 4872–4879, Aug. 15, 1990; *Cancer* 67: 2880–2886, 1991; *Cancer Res.* 50: 1291–1298, 1990; *Biotechnology*, 3: 378–384, 1985; *Proc. Nat'l Acad. Sci. USA*, 78: 3199–3203, 1981; *Cancer Res.*, 48: 6811–6818, 1988; *Cancer Res.*, 48: 2214–2220, 1988; *J. Nat'l Canc. Inst.* 1986:6666): 995–1003; *Int'l J. Cancer* 1982: 29: 539–545; *Int'l J. Cancer* 1983: 31: 543–551; *Cancer Res.*, 50: 6987–6994, 1990; *Cancer Res.*, 51: 2889–2896, 1991; *J. Clin. Lab. Anal.*, 4: 465–473, 1990; *Cancer Res.*, 51, 6363–6371, Dec. 1, 1991; *J. Nat'l Cancer Inst.* 82: 1191–1197, 1990; *Cancer Res.* 51, 5378–5383, Oct. 1, 1991); CC83, another second generation B72.3 anti-TAG antibody; CEA antibodies such as $A_5B_7$ monoclonal antibody (*Cancer Research Campaign Technology*, Ltd, London, England) (see *Int. J. Cancer*, 47: 597–602, 1991; *Br. J. Cancer*, 54:75–82, 1986; *Br. J. Cancer*, 61: 891–894, 1990; *Int. J. Cancer, Supplement* 3, 34–37, 1988; *Eur. J. Nucl. Med*, 13: 197–202, 1987; *Br. J. Cancer*, 60: 549–554, 1989; and *Br. J. Cancer*, 61: 659–662, 1990); monoclonal antibody B17-1A and its F(ab')$_2$ fragment (Wistar Institute, Philadelphia, Pa.); and monoclonal antibody 19-9 and its F(ab')$_2$ fragment (Centocor, Inc., Philadelphia, Pa.).

With respect to the radiolabel of choice, the ability to use a radiation detection probe that can be placed in immediate adjacency to the lymph node means that lower level energy isotopes are preferred, especially those exhibiting photon emissions of energy levels less than about 550 kev, advantageously less than about 300 kev, and preferably less than about 150 kev. $^{125}$I currently is the isotope of choice, though additional low energy isotopes as disclosed in the '840 patent may be used as is necessary, desirable, or convenient. Higher energy level radioisotopes (e.g., $^{131}$I) also may be used, though suitable collimation of the radiation detection probe must be employed which may impede the instrument being facile to the surgeon and limit the areas within the body cavity which can be suitably surveyed.

In addition to radioisotopes emitting gamma radiation, radioisotopes exhibiting beta radiation additionally can be used in conjunction with a probe which can detect beta radiation or positrons. The detection of beta radiation intraoperatively is disclosed, for example, in U.S. Pat. No. 5,008,546, the disclosure of which is expressly incorporated herein by reference.

The dosage of labeled locator is such that the radiation detection probe can be utilized for determining lymph node sites exhibiting accretion of the radiolabeled locator. Such dosages depend upon the specific type of label, the type of locator, and like factors which may affect dosage requirements as those skilled in the art will appreciate.

With respect to the detection of lymph node sites exhibiting accretion of the radiolabeled locator, reference is made to the following patents which show a preferred hand-held probe for the detection of gamma radiation: U.S. Pat. Nos. 4,801,803, 4,889,991, and 5,070,878, the disclosures of which are expressly incorporated herein by reference. As stated above, U.S. Pat. No. 5,008,546 discloses a probe suitable for the detection of beta radiation. Additional radiation detection devices can be used as is necessary, desirable, or convenient. In this regard, it will be appreciated that intraoperative accessing of the patient in order to determine lymph node involvement is but one alternative for practice of the present invention. Additionally, probes may be used as part of an laproscope, mediastinoscope, or like specific instrument which suitably can be outfitted with a miniaturized radiation detection device which can be placed in immediate adjacency with the lymph node in order to determine accretion of radioactivity. Regardless of the instrument or technique employed, the present invention encompasses all such instruments and techniques, by whatever label.

As is reported in the '840 patent, the immediate accession of the patient with the radiation detection probe is not advisable. Preferably, time is permitted to elapse following administration of the radiolabeled locator in order for unbound radiolabeled locator to be cleared from the tissue surrounding the lymph nodes to be surveyed. Suitable radiation detection probes function by determining a level of radioactivity over and above that normal background radioactivity found at the location (e.g., operating room) where the patient is being surveyed as well as the blood pool background (radiolabeled locator circulating in the blood stream), and surrounding tissue which may contain circulating unbound radiolabeled locator. The time may be as short as a few minutes on up to several weeks, depending upon how fast the patient's body clears (often metabolizes) the radiolabeled locator. Of importance is the recognition that the radiolabeled locator will be bound to the tumor cell site with its radiolabel intact, albeit at reduced levels, after such time period has elapsed. Importantly, it is inappropriate to survey the lymph nodes based upon maximum tumor uptake of the radiolabeled locator as is traditionally taught in external scintigraphy and external imaging technology.

Once the suitable interval has elapsed, the patient is accessed with the radiation detection probe and lymph node sites are surveyed with the probe for determining accretion of radiolabeled locator by detecting with the probe elevated levels of radiation at the lymph node sites. Besides the determination of micrometastatic tissue which may alter the course of surgical treatment as disclosed in the '840 patent, the present invention now enables the physician to determine lymph nodes which are enriched in CD4+ lymphocytes for use in preparing a therapeutic agent for the regression of neoplastic tissue (cancer).

The determined lymphocyte cells then are expanded or proliferated in a manner that importantly departs from conventional cell expansion in prior immunotherapy procedures. Briefly, cell expansion involves the steps of dissociation of LNL from lymph node tissue; ex vivo activation and initiation of cell expansion; media changes, cell culture splitting, and weaning from exogenous cytokines; and cell harvest and preparation of final product for administration to the patient.

Cell and tissue dissociation is accomplished conventionally, such as by centrifugation, in order to harvest the LNLs. Initiation of cell expansion includes the initial use of serum-free Macrophage SFM media which is unique to this cell expansion regimen. Additionally, mitogenic stimulation most preferably is conducted using IL-2 and soluble anti-$CD_3$ cells which are simultaneously added (rather than sequential addition and the use of plate-bound anti-$CD_3$ cells, as in the art). Aliquots of fresh media and cytokine are periodically added to the culture during their growth. Importantly, the cells are weaning from exogenous cytokines (e.g., IL-2) by incorporating only fresh media so as to lower the amount of IL-2, say, to less than 20 Cetus units/mL of culture. It is believed that by weaning the cells from exogenous cytokines, the need for additional cytokine administration to the patient along with the LNL cells is obviated, and the data will confirm this.

The details of a typical cell expansion regimen are set forth below:

Day 0

Media for ex vivo cell growth is aseptically prepared using prepackaged 10 L media dispensing bags of serum-free Macrophage SFM media containing 50 $\mu$g/mL gentamicin. Conical tubes containing washed lymph node lymphocytes from the cell and tissue dissociation processes are gently inverted several times to mix cells. Cells are mixed, and a 1 mL aliquot is removed for counting. Based on cell concentration, IL-2, and anti-$CD_3$ are added to the cell suspension in an amount that will achieve a concentration in the added media of 100 Cetus units/$10^6$ cells of IL-2 (Chiron Corp., Emeryville, Calif.) and 100 ng/$10^6$ cells anti-$CD_3$ (OKT3, Johnson and Johnson, Raritan, N.J.).

The cell suspension containing the IL-2 and OKT3 is transferred using a 60 cc sterile syringe to a 1 L sterile gas permeable culture bag containing the complete media so that the final cell concentration is 1×$10^6$ cells/mL. Cells are now contained within a closed culture system and will remain in a closed system until the end of the 10-day culture period.

Cell culture bags are labeled with patient identification markings and then placed into a 37° C. humidified incubator containing 7% $CO_2$.

Day 4

Four days after initiation of the incubation period, the cell culture bags are removed from the incubator. The bag is gently kneaded to disperse cells into solution. Using a sterile syringe to enter the sampling port of the culture bag, a 5 mL aliquot is removed for counting, viability, and morphology analyses.

The final volume of fresh complete media and cell suspension to be added to each fresh 1 L culture bag is calculated on the basis of a final concentration per bag of 0.25×$10^6$ cells/mL. A concentration of 300 Cetus units of IL-2 units for every $10^6$ cells is added to the culture bag containing the cell suspension so that a final concentration of 100 Cetus units/mL IL-2 is achieved in each fresh 1 L culture bag.

Cells culture bags are now prepared for transfer into fresh media and fresh sterile gas-permeable culture bags. Using a DuPont SCD sterile tubing welder, a closed transfer line is created between the sterile pump tubing set-up, the culture bag containing the cell suspension, the fresh complete media bag, and the sterile bags to which media and cells will be transferred. The pump tubing is threaded into the cam of a peristaltic pump and volumes for suspension and fresh complete media additions are set. The pump is turned on and the contents of the cell suspension bag and fresh media are distributed between the predetermined number of fresh culture bags.

Once the transfer is completed, sterile tubing seals are welded for each bag. Bags are labeled with patient identification markings. All bags are returned to the 37° C., 7% $CO_2$ humidified incubator. All original culture bags are discarded in accordance with institutional guidelines for medical wastes.

Day 7

Seven days from the initial start of the culture period, the cells are again mixed by gentle kneading. A 5 mL aliquot is removed from one of the culture bags and analyzed for cell number, viability, and morphology. On the basis of the cell count, fresh media and cell suspension volumes are calculated to achieve a final concentration of $0.5 \times 10^6$ cells/mL in the fresh iL culture bags. Forty (40) Cetus units/$10^6$ cells of IL-2 are added to the fresh complete media resulting in a 20 Cetus units/mL IL-2 as the final concentration in each culture bag to which media and cell suspension are transferred.

Cells and fresh media are transferred to fresh gas permeable bags using the peristaltic pump and sterile tubing welder set-ups as described previously. Once transfer and seals are completed, bags are labeled and placed in the 37° C., 7% $CO_2$ humidified incubator.

Day 9

Twenty-four hours prior to preparation of cells for patient infusion, a 10 mL aliquot from 10% of the bags is removed for aerobic and anaerobic microbiological analysis.

Patient Infusion Preparation

Day 10

On the 10th day of the culture period, culture bags are removed from the incubator for the removal of media, pooling of the cells from each of the culture bags, and the concentration of cells. Depending on the number of bags, this process may take from 45 minutes to 2 hours. Each 1 L culture bag is processed at a rate of 250 mL/minute using a Stericell processor and collection bowl. Bag tubing is threaded into the cams of the processor and the pump and centrifuge are turned on. Cells are concentrated in the processor bowl and waste media is pulled off and discarded.

After all culture bags have been pooled and the media removed, approximately 950 mL of 1.25% USP human albumin in sterile saline are washed through the cells to remove any remaining culture media The flow of the Stericell pump is reversed and approximately 270 mL of cells are pumped into a sterile 500 mL transfer pack. The processor bowl is rinsed into the transfer pack using 50 mL of the albumin and saline mixture. The final cell concentration of this transfusion preparation is $1-5 \times 10^{10}$ cells. This preparation is labeled with the appropriate patient identification.

An aliquot of 1 mL for quality control (QC) testing is removed from the transfusion bag using a sterile syringe. The transfusion bag is then stored at 2°–8° C. until all QC testing is completed. The patient transfusion preparation is delivered to the attending physician after satisfactory results are reported from the QC testing.

Manufacturing Process Controls

Overall OC Program

The Quality Control program is designed to ensure both the quality of material used in manufacturing and the final product.

Additional controls include assurance of patient cell identification throughout the manufacturing process. All cell culture containers for a given patient are segregated from other patient cells and are clearly labeled with specific patient identification markings. Each patient is assigned to an incubator dedicated to their own cells that is not shared with any other patient during the 10 day incubation period.

Open cell culture manipulations are minimal and when required, during initial culture set-up, are performed under aseptic conditions in a laminar flow hood. The majority of processes including cell culture splitting and transfers are conducted in a closed culture system to preclude contamination.

Cell Culture OC Testing

At days 0, 4, 7, and 10, cell culture samples are aseptically collected and analyzed for viability, cell number, and morphology. Viability and cell numbers are assessed using blue staining techniques. Morphology is performed with microscopic review of cytospin preparations using Wrights-Giemsa staining.

Twenty-four (24) hours prior to patient infusion, both aerobic and anaerobic bacterial cultures are performed using BACTec blood culture reagents. Immediately before patient infusion, a Gram stain is performed and endotoxin testing using an FDA licensed commercial test is conducted.

The transfusion preparation of expanded, activated cells must be negative for the Gram stain, show a cell viability $\geq 70\%$, and have a measured LAL level of <1.0 EU/mL.

Desirably, about $10^{10}$ cells are produced for administration to the patient. Autologous expanded cells presently are preferred for use in administering to the patient from which the lymph nodes were removed. Preferably, also, neoplastic tissue judged by the surgeon to be resectable is removed along with the determined lymph nodes. Administration of the therapeutic agent thereafter is accomplished. For those patients whose involvement is non-resectable, the determined lymph nodes only are removed, expanded, and the resulting therapeutic agent administered.

Initial data generated and reported herein was gathered in accordance with the following experimental procedures.

EXAMPLE I

Initial Experimental Procedures

Patient Selection and RIG® Probe System

Patient selection and RIGS® probe system eligible patients had documented colorectal cancer, either recurrent disease or primary cancer. All patients entered in the study underwent an extensive preoperative evaluation to eliminate, when possible, those patients with extra-abdominal tumor. Preoperative evaluation included CT scans of the chest, abdomen, and pelvis, as well as a bone scan when deemed necessary. CEA tests and colonoscopy also were part of the preoperative evaluation. All patients signed an Institutional Review Board Written Consent. Two days before the administration of the radiolabeled antibody, the patient began treatment with an oral solution of potassium iodide (SSKI at 10 drops twice a day, or KI at 500 mg twice a day) to block uptake of radiolabeled CC49 monoclonal antibody by the thyroid, and this regimen continued for three weeks or until surgery. The CC49 MoAb was radioiodinated using the Iodogen method performed in the nuclear pharmacy at The Ohio State University (OSU) Medical Center. Once the negative skin test with unlabelled antibody was confirmed, the patient received by intravenous injection 0.1 mg of the CC49 MoAb label with 1 mCi of iodine-125 ($^{125}I$) diluted in 4 ml phosphate buffered saline and infused for five minutes. All patients were observed for one hour after injection with vital signs recorded every 15 minutes for one hour. Patients were scheduled for surgery when the precordial counts determined by the gamma detecting probe (GDP), Neoprobe® RIGS® 1000 instrument were less than 20 counts per 2 seconds. Serum samples were obtained before injection at the surgery.

The operative procedure involved a thorough laparotomy using the Neoprobe® RIGS® 1000 instrument, the details of which have been previously described. At the time. of surgery, lymph nodes were probed in the gastrohepatic ligament, periportal region, celiac nodes, suprapancreatic region, and mesenteric nodes to find lymph nodes which were RIGS® probe-positive. RIGS® probe-positive tissue is determined by a tissue to background ratio of greater than 1.5:1. Various lymph nodes were harvested from the patients as well as a sample of tumor tissue. These materials were sent in buffered saline immediately to the pathology department All material was examined by a pathologist. Tissues were treated sterilely.

All lymph nodes used were bisected longitudinally and half was sent to the lymph node laboratory and the other half was kept for routine hematoxylin and eosin (H&E) histologic evaluation. The pathologist examined all dissected nodes. The tumor tissues were examined by the pathologist and small pieces less than a few centimeters were removed and placed in sterile saline and transported to the lymph node laboratory. Routine pathology, including hematoxylin and eosin staining, was performed on all patient material received.

Preparation of Lymphocytes

On the day of surgery, blood was obtained from the patient and a Ficoll-Hypaque (Pharmacia) separation performed to obtain peripheral blood mononuclear cells (PBMC). These cells were washed and resuspended in RPMI 1640 to which was added, Penicillin (100 units/ml), Streptomycin (100 $\mu$g/ml), and 10% human sera, type AB (GIBCO, mycoplasma tested). This was complete RPMI (RPMIc). If splenocytes were to be used, the spleen tissue was minced gently into RPMIc. The resulting cell suspension was processed with a Ficoll-Hypaque separation as above. If these lymphocytes were to be used as stimulator cells, they were exposed to 4000 rads (Cesium source) prior to plating in mixed lymphocyte culture.

The lymph nodes were kept on ice in sterile media until processed and were prepared by gently mincing the node into RPMIc. The cell suspension was centrifuged and pellet washed in RPMIc. Viability was determined by blue exclusion before each assay. Viability was routinely greater than 95%. Analysis for $CD_4+$ and $CD_8+$ lymphocyte was performed using an Epics ELITE flow cytometer from Coulter. LNLs were stained using a dual staining reagent T4-FITC/T8-PE (Olympus). Cells ($5 \times 10^5$/tube) were resuspended in 0.1 ml PBS (1% fetal calf serum) and incubated 20 minutes in 10 ul T4/T8 staining reagent at room temperature in the dark. They were washed twice in additional PBS, fixed with 0.5 mls PBS buffered 1% formalin, and stored in the dark at 4° C. until analyzed using the flow cytometer.

Preparation of Tumor Samples

The excised tumor was stored in sterile saline on ice to maintain viability. After removing the necessary tissue for pathology, the tumor is washed in RPMI without sera (RPMIic) and placed in a petri dish where it was minced into pieces 1 to 1.5 mm in size. The minced tumor was transferred to a 50 ml conical centrifuge tube where the tissue was rinsed in additional RPMIic. All but 5 ml to 10 ml of the media was removed and an equal volume of 0.4% type 1 collagenase (SIGMA) prepared in PBS was added to the tube. This digestion was allowed to incubate for one hour at 37° C. The tube was vortexed every 15 minutes to aid in cell dispersion. After incubation, RPMIc was added to equal 45 mls aliquots thereof. The undigested tumor was allowed to settle out and the cell suspension carefully removed from the top of the tube. The cells were centrifuged at 400× g for 15 minutes. The remaining tumor was left in the tube and then subjected to an additional digestion. After the tumor cell pellet was washed 2× in RPMIc, the viability was determined by blue exclusion. If the tumor cells were to be used in a proliferation assay, they were exposed to 3000 rads (cesium source) before plating. Residual viable tumor suspensions were maintained as a frozen tumor bank to be used as allogeneic cells in future experiments.

Tumor Cell Lines

Tumor cells were grown in minimum essential media with Earle's salts to which was added: L-glutamine 2 mM, non-essential amino acids, sodium pyruvate 0.1 mM, MEM vitamin solution, and 15% fetal calf sera (all from GIBCO). Glio is a human glioma tumor line. CAR-1 is a carcinoid tumor obtained from a patient undergoing hepatic transplant for metastatic carcinoid and was processed using the same procedure as for colon cancer cells. WD124 (a colon carcinoma cell line) was isolated from a patient with recurrent colon cancer during a RIGS® procedure. If these passaged cell lines were used in a mixed lymphocyte/tumor assay, they were exposed to 30,000 rads (cesium source) before plating.

Mixed Tumor Lymphocyte Assay

IL2 was used at the concentration of 20 $\mu$g/ml. Anti-$CD_3$ is a mouse anti-human antibody (See Yoshizawa, et al, "Activation of Anti-$CD_3$ of Tumor-Draining Lymph Node Cells for Specific Adoptive Immunotherapy", *Cellular Immunology*, 134, 473–479, 1991). The mixed tumor lymphocyte culture experiments were performed in a 96 well, round bottom tissue culture plate. RPMIc was used throughout the assay as the diluent of agents and cells with a final volume per well of 0.2 mls. Controls for all groups were included, consisting of lymphocytes or tumor cells alone, lymphocytes with tumor cells, each of the above with IL-2, and mixed cultures with IL-2 as well as a dose response of anti-$CD_3$. Lymphocytes were plated at a density of $1 \times 10^4$ per well and tumor at $5 \times 10^3$ per well. The plates were incubated for 96 hours at 37° C. in a humidified $CO_2$ incubator (5% $CO_2$). After this period, 1 uCi per well of [$^3$H] thymidine (ICN, specific activity, 6.7 Ci/mmol) was added for 18 hours. A cell harvester (PHD) was used in conjunction with glass fiber filter strips to harvest the wells. The punched filter discs were dropped into vials and an aqueous scintillation cocktail was added before counting in a Beckman 1801 scintillation counter. Statistical analysis using the student's t test was employed to determine significance.

Initial Experimental Results

When Type I LNL are co-cultured in a mixed tumor lymphocyte culture with autologous (irradiated) tumor in the presence of IL-2 and anti-$CD_3$, there is a 3 to 10 fold increase in proliferation of the lymphocytes as measured by [$^3$H] thymidine incorporation as can be seen by viewing FIG. 1 and the data in Table 2 below.

TABLE 2

| Line No. | Culture Type | Anti-$CD_3$ (ng/ml) | Counts Per Minute |
|---|---|---|---|
| 10 | LNL + IL-2 + Anti-$CD_3$ | 1 | 977 |
| 10 | LNL + IL-2 + Anti-$CD_3$ | 10 | 2414 |
| 10 | LNL + IL-2 + Anti-$CD_3$ | 50 | 3217 |
| 10 | LNL + IL-2 + Anti-$CD_3$ | 100 | 2675 |
| 12 | Auto + LNL + IL-2 + Anti-$CD_3$ | 1 | 1827 |
| 12 | Auto + LNL + IL-2 + Anti-$CD_3$ | 10 | 8051 |
| 12 | Auto + LNL + IL-2 + Anti-$CD_3$ | 50 | 9412 |
| 12 | Auto + LNL + IL-2 + Anti-$CD_3$ | 100 | 8920 |
| 14 | Allo + LNL + IL-2 + Anti-$CD_3$ | 1 | 1843 |
| 14 | Allo + LNL + IL-2 + Anti-$CD_3$ | 10 | 5802 |
| 14 | Allo + LNL + IL-2 + Anti-$CD_3$ | 50 | 5803 |
| 14 | Allo + LNL + IL-2 + Anti-$CD_3$ | 100 | 5789 |
| 16 | Auto PBLs + LNL + IL-2 + Anti-$CD_3$ | 1 | 996 |
| 16 | Auto PBLs + LNL + IL-2 + Anti-$CD_3$ | 10 | 1937 |
| 16 | Auto PBLs + LNL + IL-2 + Anti-$CD_3$ | 50 | 3201 |
| 16 | Auto PBLs + LNL + IL-2 + Anti-$CD_3$ | 100 | 3270 |
| 18 | Allo PBLs + LNL + IL-2 + Anti-$CD_3$ | 1 | 1317 |

TABLE 2-continued

| Line No. | Culture Type | Anti-CD$_3$ (ng/ml) | Counts Per Minute |
|---|---|---|---|
| 18 | Allo PBLs + LNL + IL-2 + Anti-CD$_3$ | 10 | 2324 |
| 18 | Allo PBLs + LNL + IL-2 + Anti-CD$_3$ | 50 | 2665 |
| 18 | Allo PBLs + LNL + IL-2 + Anti-CD$_3$ | 100 | 3729 |

The proliferation occurs only if the lymphocytes are activated with anti-CD$_3$ and low concentrations of IL-2 (20 U/ml). These LNL respond in various degrees to allogeneic human colon cancer cells as the foregoing data demonstrates. The LNL proliferate only modestly to tumor cells in the presence of IL-2 alone, and often, no significant proliferation can be seen with IL-2 and tumor cells alone compared with the proliferation seen with IL-2 and anti-CD$_3$.

Figure 2:
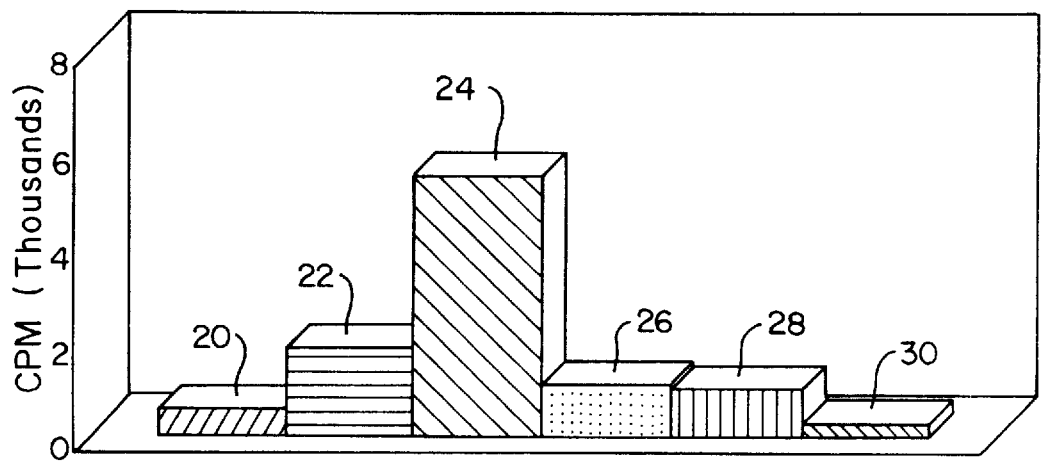
FIG. 2 graphically displays the comparison of IL-2 and anti-CD$_3$ to IL-2 in stimulating mixed tumor lymphocyte culture in Type I LNL. This same data is displayed in Table 3. Type I LNL ($10^4$ cells) were cultured with irradiated autologous tumor ($5\times10^3$), in the presence of various concentrations of IL-2 alone, or IL-2 (20 $\mu$g/ml) and anti-CD$_3$ (50 ng/ml). Cultures were pulsed with [$^3$H] thymidine after 96 hours and harvested 18 hours later. Counts were determined by liquid scintillation counting.

Even high concentrations of IL-2 (100 or 500 µg/ml) did not stimulate proliferation as well as low concentrations of IL-2 with anti-CD$_3$, as the data in FIG. 2 and Table 3 below demonstrate.

TABLE 3

| Line No. | Culture Type | IL-2 (ug/ml) | Anti-CD$_3$ (ng/ml) | Counts Per Minute |
|---|---|---|---|---|
| 20 | LNL + IL-2 | 20 | 0 | 558 |
| 22 | LNL + IL-2 + Anti-CD$_3$ | 20 | 50 | 1793 |
| 24 | Auto + LNL + IL-2 + Anti-CD$_3$ | 20 | 50 | 5398 |
| 26 | Auto + LNL + IL-2 | 20 | 0 | 1070 |
| 28 | Auto + LNL + IL-2 | 100 | 0 | 986 |
| 30 | Auto + LNL + IL-2 | 500 | 0 | 277 |

The Type I lymph nodes contain between about 40% and 70% of CD4+ lymphocytes and about 8% to 15% CD8+ lymphocytes. It has been shown with PBL that IL-2 and anti-CD$_3$ can stimulate proliferation of CD4+ and CD8+ lymphocytes, but IL-2 alone does not stimulate CD4 lymphocyte proliferation. Nishimura, et al., "Generation, Propagation, and Targeting of Human CD4+ Helper/Killer T-cells Induced by Anti-CD$_3$ Monoclonal Antibody Plus Recombinant IL-2. An Efficient Strategy for Adoptive Tumor Immunotherapy.", *J. Immunol.*, 148:285–291, 1992. It may be that with high percentages of CD4+ lymphocytes in the Type I nodes, anti-CD$_3$ and IL-2 may stimulate these cells which the IL-2 alone cannot.

Figure 3:
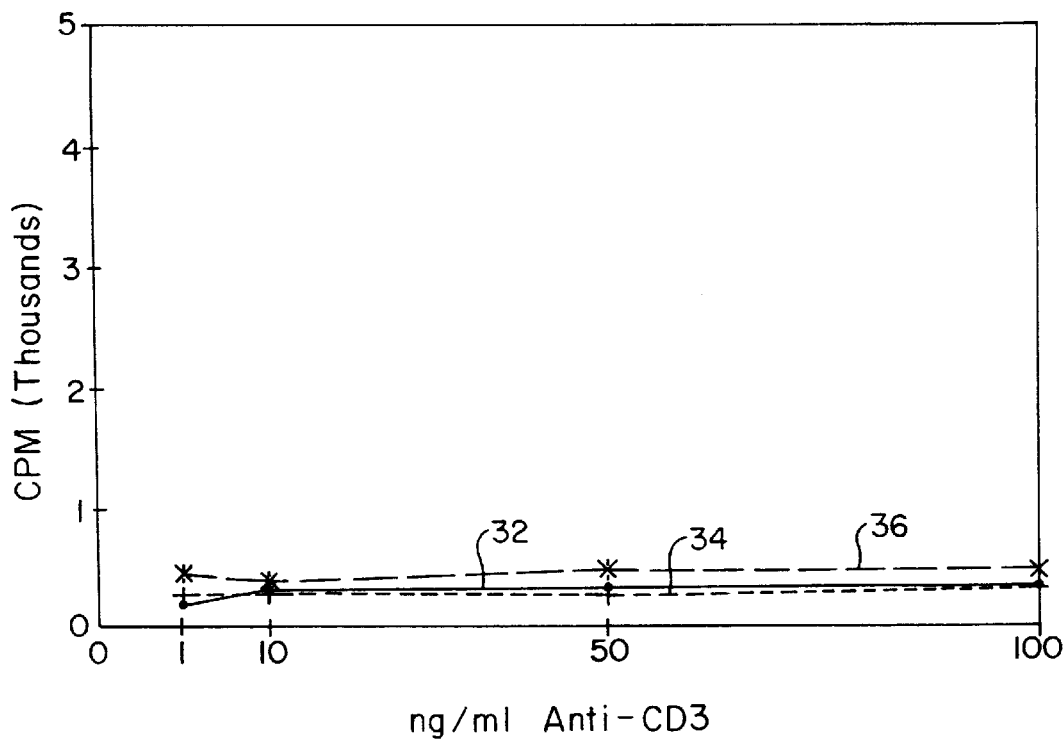
FIG. 3 graphically displays mixed tumor lymphocyte cultures of Type III LNL. This same data also is displayed in Table 4. LNL ($10^4$ cells) were cultured 96 hours in the presence of autologous or allogeneic ($5 \times 10^3$, 4000 rads) human colon carcinoma cells and IL-2 (20 µg/ml) as well as various concentrations of anti-$CD_3$. Cells were harvested 18 hours after addition [$^3$H] thymidine (1 uCi/well) and thymidine incorporation determined by liquid scintillation counting.

In contrast to Type I lymph nodes, Type III LNL did not proliferate in response to autologous tumor, allogeneic tumor, or a combination of IL-2 and anti-CD$_3$, as can be seen by reference to FIG. 3 and Table 4 below.

TABLE 4

| Line No. | Culture Type | Anti-CD$_3$ (ng/ml) | Counts Per Minute |
|---|---|---|---|
| 32 | LNL + IL-2 + Anti-CD$_3$ | 1 | 192 |
| 32 | LNL + IL-2 + Anti-CD$_3$ | 10 | 310.8 |
| 32 | LNL + IL-2 + Anti-CD$_3$ | 50 | 308.6 |
| 32 | LNL + IL-2 + Anti-CD$_3$ | 100 | 311 |
| 34 | Auto + LNL + IL-2 + Anti-CD$_3$ | 1 | 270.9 |
| 34 | Auto + LNL + IL-2 + Anti-CD$_3$ | 10 | 279.5 |
| 34 | Auto + LNL + IL-2 + Anti-CD$_3$ | 50 | 246.7 |
| 34 | Auto + LNL + IL-2 + Anti-CD$_3$ | 100 | 286.7 |
| 36 | Allo + LNL + IL-2 + Anti-CD$_3$ | 1 | 439.7 |
| 36 | Allo + LNL + IL-2 + Anti-CD$_3$ | 10 | 382.4 |

TABLE 4-continued

| Line No. | Culture Type | Anti-CD$_3$ (ng/ml) | Counts Per Minute |
|---|---|---|---|
| 36 | Allo + LNL + IL-2 + Anti-CD$_3$ | 50 | 470.5 |
| 36 | Allo + LNL + IL-2 + Anti-CD$_3$ | 100 | 446.3 |

The reason for this lack of tumor immune activity as far as proliferation is not clear since tumor-containing nodes have been a source of TILL cells. Schwartzentruber, et al., "Specific Release of Granulocyte-Macrophage Colony-Stimulating Factor, Tumor Necrosis Factor Alpha, and Gamma Interferon by Human Tumor-Infiltrating Lymphocytes After Autologous Stimulations", *J. Immunol.*, 146:3674–3681, 1991. The assays for the growth of TIL cells, however, require long-term culture and high concentrations of IL-2, and the LNL assays reported herein are short-term, four-day assays in fresh cultures.

Figure 4:
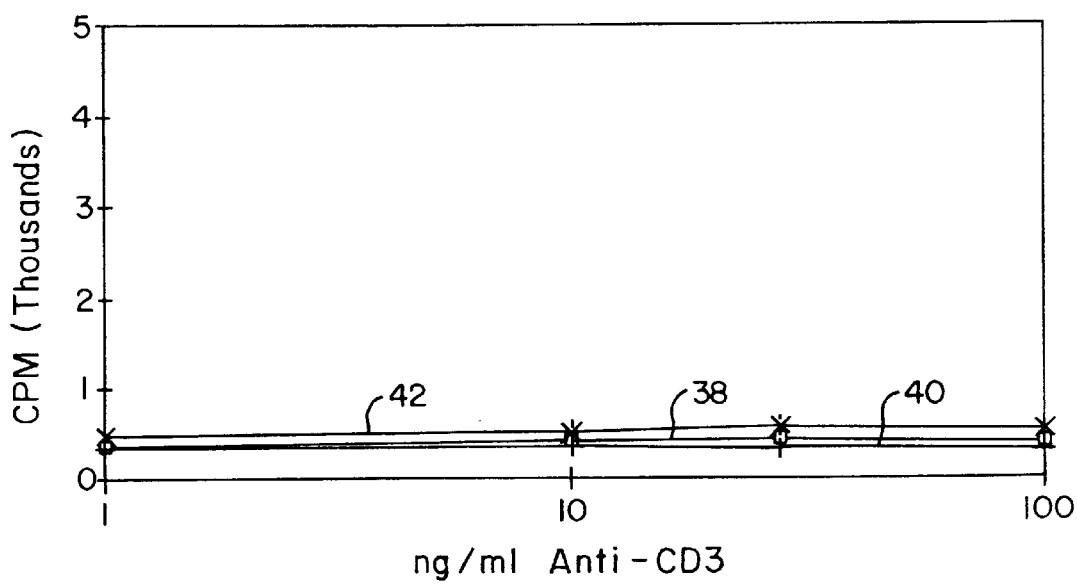
FIG. 4 graphically displays mixed tumor lymphocyte culture of Type 0 LNL. This same data also is displayed in Table 5. LNL ($10^4$/well) were cultured 96 hours with autologous or allogeneic human colon carcinoma cells ($5 \times 10^3$/well, 4,000 rads) with 20 µg/ml IL-2 and various concentrations of anti-$CD_3$. After 96 hours [$^3$H] thymidine was added (1 uCi/well), and 18 hours later the plates were harvested and thymidine incorporation determined by liquid scintillation counter.

Type 0 lymph node lymphocytes vary in their response, most demonstrate very little tumor-specific proliferation to allogeneic or autologous tumor in the presence of IL-2 and anti-CD$_3$, as can be seen by reference to FIG. 4 and Table 5 below.

TABLE 5

| Line No. | Culture Type | Anti-CD$_3$ (ng/ml) | Counts Per Minute |
|---|---|---|---|
| 38 | LNL + IL-2 + Anti-CD$_3$ | 1 | 359.1 |
| 38 | LNL + IL-2 + Anti-CD$_3$ | 10 | 421 |
| 38 | LNL + IL-2 + Anti-CD$_3$ | 50 | 406 |
| 38 | LNL + IL-2 + Anti-CD$_3$ | 100 | 376.2 |
| 40 | Auto + LNL + IL-2 + Anti-CD$_3$ | 1 | 327.6 |
| 40 | Auto + LNL + IL-2 + Anti-CD$_3$ | 10 | 357.2 |
| 40 | Auto + LNL + IL-2 + Anti-CD$_3$ | 50 | 321 |
| 40 | Auto + LNL + IL-2 + Anti-CD$_3$ | 100 | 321.5 |
| 42 | Allo + LNL + IL-2 + Anti-CD$_3$ | 1 | 476.7 |
| 42 | Allo + LNL + IL-2 + Anti-CD$_3$ | 10 | 491.1 |
| 42 | Allo + LNL + IL-2 + Anti-CD$_3$ | 50 | 563.4 |
| 42 | Allo + LNL + IL-2 + Anti-CD$_3$ | 100 | 504.8 |

Figure 5:
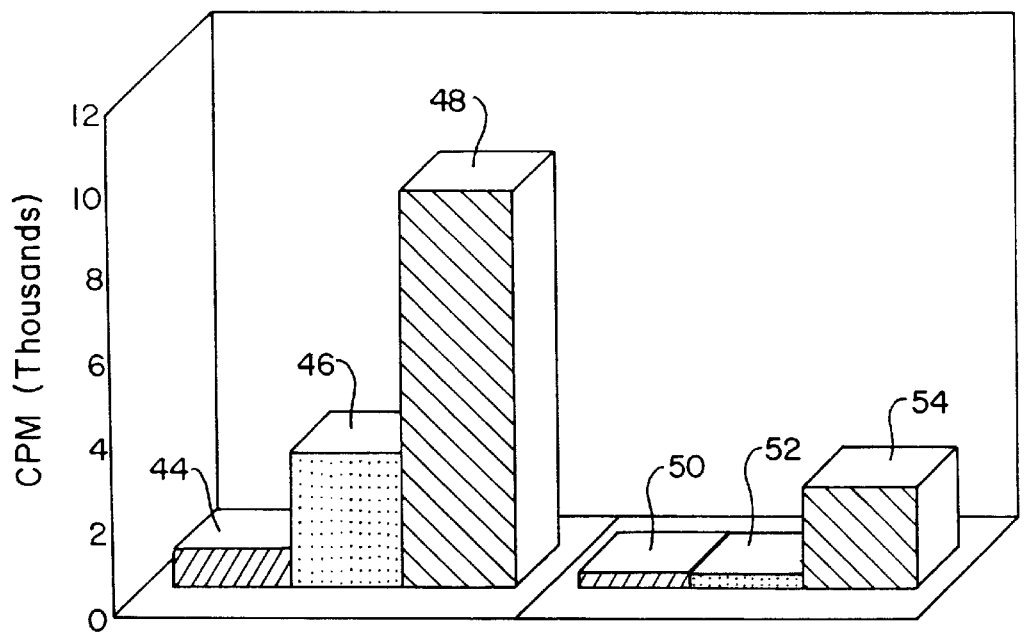
FIG. 5 graphically displays the comparison of Type I LNL with Type 0 LNL from the same patient with colorectal cancer. This same data also is displayed graphically in Table 4. Type I and Type 0LNL ($10_4$/well) were cultured 96 hours in the presence of autologous colon carcinoma cells ($5 \times 10^3$/well, 4,000 rads) with 20 µg/ml IL-2 and anti-$CD_3$ (50 ng/ml). After 96 hours the [$^3$H] thymidine was added 1 uCi/well and the plates were harvested 18 hours later.

Only about 25% to 30% of Type 0 nodes selected proliferate significantly to tumor, compared with >90% significant proliferation of Type I nodes. There were Type 0 nodes taken from patients who also have Type I nodes that did show tumor-specific proliferation; however, the amount of proliferation seen on a cell basis always is much less than can be seen in Type I lymph nodes, as can be seen by reference to FIG. 5 and Table 6 below.

TABLE 6

| Line No. | Culture Type | Node Type | Counts Per Minute |
|---|---|---|---|
| 44 | LNL + IL-2 | 0 | 364 |
| 46 | LNL + IL-2 + Anti-CD$_3$ | 0 | 345 |
| 48 | LNL + Auto + IL-2 + Anti-CD$_3$ | 0 | 2398 |
| 50 | LNL + IL-2 | I | 912 |
| 52 | LNL + IL-2 + Anti-CD$_3$ | I | 3217 |
| 54 | LNL + Auto + IL-2 + Anti-CD$_3$ | I | 9412 |

These results suggest that the invention is useful in selecting lymph nodes with tumor-specific activity.

Figure 6A:
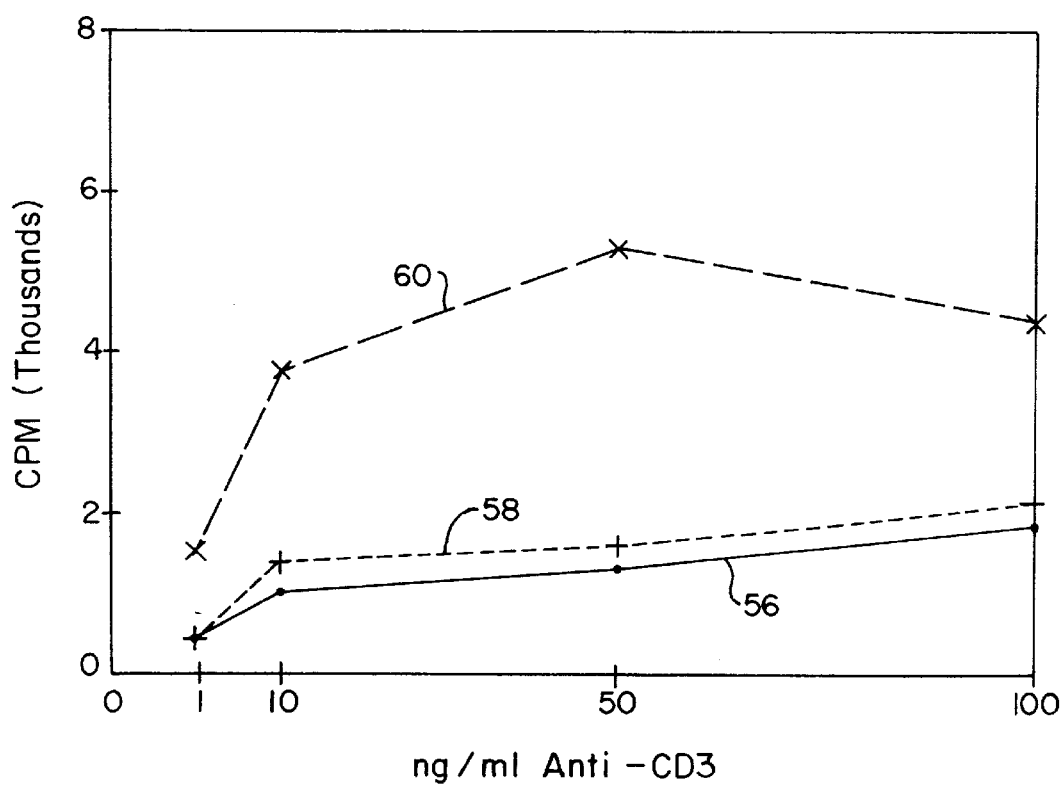
FIGS. 6A and 6B graphically display mixed tumor lymphocyte cultures of Type I and Type III splenocytes. This same data also is displayed in Table 6. Splenocytes (10$_4$ cells/well) were incubated 96 hours in the presence of autologous or allogeneic colon carcinoma cells ($5 \times 10^3$/well, irradiated cells). In the case of the Type III splenocytes, two allogeneic tumors were used. The cultures all contained 20 µg/ml IL-2 and various concentrations of anti-$CD_3$. After 96 hours [$^3$H] thymidine 1 uCi/well was added, and 18 hours later the plates were harvested and thymidine incorporation determined.
Figure 6B:
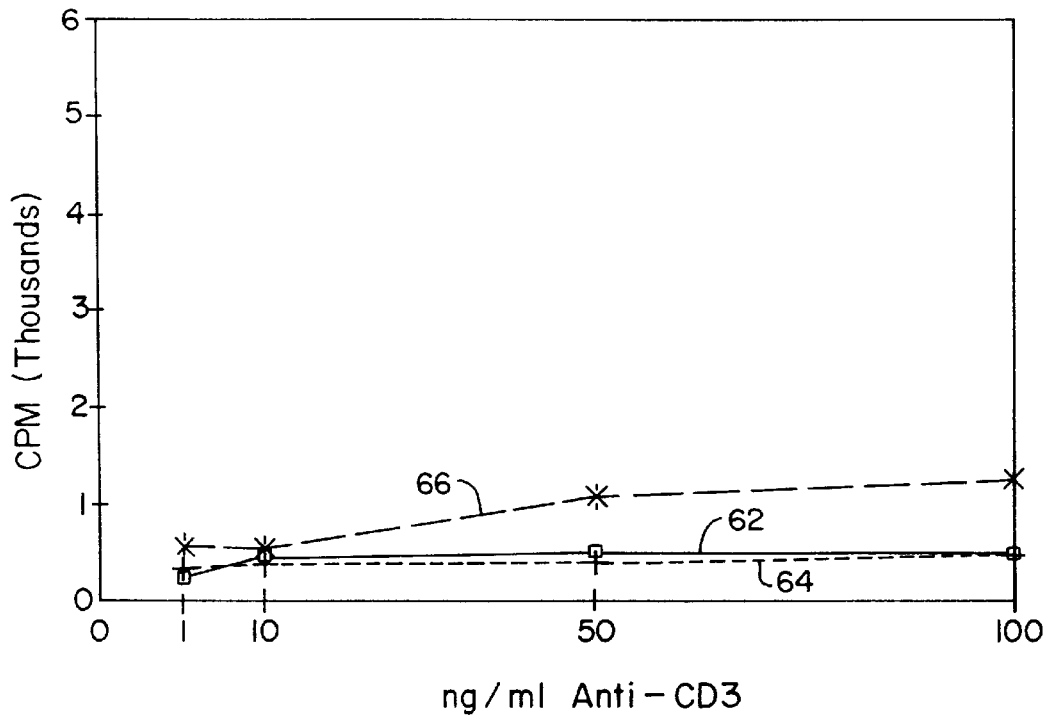

Splenic lymphocytes have the same response as is seen with LNL, i.e. Type I splenic lymphocytes proliferate in response to colonic tumors and Type III splenic lymphocytes do not, as can be seen by reference to FIGS. 6A and 6B, and Table 7 below.

TABLE 7

| Line No. | Culture Type | Spleen Type | CD₃ (ng/ml) | Counts Per Minute |
|---|---|---|---|---|
| 56 | LNL + IL-2 + Anti-CD₃ | I | 1 | 425 |
| 56 | LNL + IL-2 + Anti-CD₃ | I | 10 | 990 |
| 56 | LNL + IL-2 + Anti-CD₃ | I | 50 | 1285 |
| 56 | LNL + IL-2 + Anti-CD₃ | I | 100 | 1831 |
| 58 | Auto + LNL + IL-2 + Anti-CD₃ | I | 1 | 426 |
| 58 | Auto + LNL + IL-2 + Anti-CD₃ | I | 10 | 1396 |
| 58 | Auto + LNL + IL-2 + Anti-CD₃ | I | 50 | 1598 |
| 58 | Auto + LNL + IL-2 + Anti-CD₃ | I | 100 | 2122 |
| 60 | Allo + LNL + IL-2 + Anti-CD₃ | I | 1 | 1504 |
| 60 | Allo + LNL + IL-2 + Anti-CD₃ | I | 10 | 3744 |
| 60 | Allo + LNL + IL-2 + Anti-CD₃ | I | 50 | 5278 |
| 60 | Allo + LNL + IL-2 + Anti-CD₃ | I | 100 | 4387 |
| 62 | LNL + IL-2 + Anti-CD₃ | III | 1 | 215.6 |
| 62 | LNL + IL-2 + Anti-CD₃ | III | 10 | 412.3 |
| 62 | LNL + IL-2 + Anti-CD₃ | III | 50 | 435.5 |
| 62 | LNL + IL-2 + Anti-CD₃ | III | 100 | 405.5 |
| 64 | Auto + LNL + IL-2 + Anti-CD₃ | III | 1 | 197 |
| 64 | Auto + LNL + IL-2 + Anti-CD₃ | III | 10 | 341 |
| 64 | Auto + LNL + IL-2 + Anti-CD₃ | III | 50 | 343 |
| 64 | Auto + LNL + IL-2 + Anti-CD₃ | III | 100 | 385 |
| 66 | Allo + LNL + IL-2 + Anti-CD₃ | III | 1 | 526.7 |
| 66 | Allo + LNL + IL-2 + Anti-CD₃ | III | 10 | 502.2 |
| 66 | Allo + LNL + IL-2 + Anti-CD₃ | III | 50 | 1012 |
| 66 | Allo + LNL + IL-2 + Anti-CD₃ | III | 100 | 1145.22 |

Most spleens exhibit probe radioactivity consistent with the presence of tumor cells; however, because few spleens are removed, there are very few data on splenic lymphocytes presently.

Figure 7:
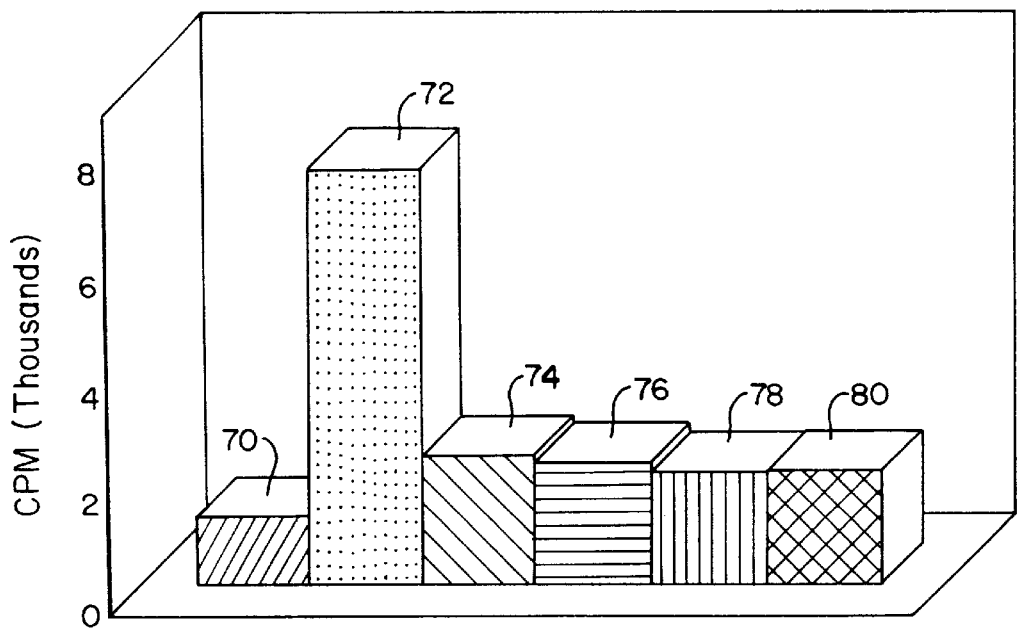
FIG. 7 graphically displays the comparison of various tumors in stimulating Type I LNL in mixed tumor lymphocyte culture. This same data also is displayed in Table 6. LNL ($10^4$/well) from Type I nodes were co-cultured in the presence of several tumors ($5 \times 10^3$/well, irradiated cells) including autologous colon cancer cells, a human glioma (Glio) cultured cell line, a human carcinoid (CAR1) tumor harvested fresh from a patient undergoing liver transplantation, a cultured human colon carcinoma cell line (WD124), and autologous PBL's with IL-2 20 µg/ml and anti-$CD_3$ (50 ng/ml). After 96 hours [$^3$H] thymidine was added (1 uCi/well) and the cells were harvested 18 hours later. [$^3$H] thymidine incorporation was determined by liquid scintillation counting. Cultures of LNL with tumor without growth factors, or any tumor cultures alone with growth factors did not stimulate proliferation. LNLs are Type I cultured with IL-2 (20 µg/ml) and anti-$CD_3$ (50 ng/ml) alone.

The LNL from Type I lymph nodes proliferate in response to both autologous and allogeneic tumors. These LNL do not proliferate against allogeneic PBL from the same donor as allogeneic colon cancer, nor do they proliferate to autologous PBL (see FIG. 1), human glioma cells, or human carcinoid tumor cells, as can be seen by the reference to FIG. 7 and Table 8 below.

TABLE 8

| Line No. | Tumor Type | CPM |
|---|---|---|
| 70 | None | 1239 |
| 72 | Auto | 7496 |
| 74 | Glio | 2340 |
| 76 | WD124 | 2208 |
| 78 | CAR1 | 2036 |
| 80 | PBL | 2002 |

Recent studies have shown that a combination of IL-2 and anti-CD₃ can stimulate proliferation of CD₄+ peripheral blood lymphocytes which IL-2 alone cannot Nishimura, et al., "Generation, Propagation, and Targeting of Human CD₄+ Helper/Killer T Cells Induced by Anti-CD₃ Monoclonal Antibody Plus Recombinant IL-2", supra. Since the Type I LNL contain greater than 50% CD₄+ lymphocytes, the use of anti-CD₃ and IL-2 may be stimulating proliferation of the CD₄+ lymphocytes as well as CD₈+ lymphocytes. Separation of CD₄+ and CD₈+ lymphocytes and the proliferation response to growth factors and tumor, thus, appears to be desirable.

In connection with the therapeutic procedures reported in Example III below, phenotypic analysis of the lymph nodes determined by the present invention was undertaken using flow cytometric analysis of lymphocytes before and after culture in IL-2 (20 μ/ml) and anti-CD₃ were taken with the following results being recorded:

TABLE 9

| Patient Node Type | Day 1 | | Day 12–16 | |
|---|---|---|---|---|
| SMC8-046 Lnode | CD4 | 63.2% | CD4 | 68.3% |
| | CD8 | 19% | CD8 | 35.4% |
| | CD3 | 79% | CD3 | 82.1% |
| | CD19 | 11.3% | CD19 | 4.4% |
| RG154 Lnode | CD4 | 51% | CD4 | 62.3% |
| | CD8 | 6% | CD8 | 29.4% |
| | CD3 | 61.7% | CD3 | 97.7% |
| | CD19 | <1% | CD19 | <1% |
| JG192 mesenteric Lnode | CD4 | 67.3% | CD4 | 43.5% |
| | CD8 | 8.9% | CD8 | 41.6% |
| | CD3 | 84.8% | CD3 | 96.9% |
| | CD19 | 3% | CD19 | <1% |
| JG196 periportal Lnode | CD4 | 61.4% | CD4 | 36.2% |
| | CD8 | 8.3% | CD8 | 45.8% |
| | CD3 | 79.6% | CD3 | 96.3% |
| | CD19 | 3.9% | CD19 | <1% |

These results demonstrate that the population of T-cells (CD₃) increased after culture. Also, these results demonstrate that CD19 cells (B cells) diminish over the culture time. It should be noted that in other studies that LNL proliferation was inhibited by the addition of anti-Class I major histocompatibility antibody (MHC) as well as anti-Class II MHC antibody.

Long term culturing of lymph node lymphocytes under different mitogenic stimulation conditions was undertaken and such expansion compared to the use of ant-CD₃ as reported for much of the foregoing data. Cultures were started on day 1 at 1×10⁶ LNL/ml RPMIc (RPMI 1640 media supplemented with HEPES buffer, 25 mM; penicillin 100 units/ml; streptomycin, 0.1 mg/ml; and re-calcified, heat-inactivated human plasma, 10%). After 4 days, cells were split to 0.25×10⁶ per ml and then passages continued in this manner. The following additions where indicated were made: IL-2,20 units/ml; anti-CD₃, 50 ng/ml; Phorbol 12-myristate 13-acetate (PMA), 2 ng/ml; and Ionomycin, 50 ng/ml. The indicated additions and cell expansions were

TABLE 10

| Patient Day | IL-2 + anti-CD₃ Fold Expansion | IL-2 + PMA + Ionomycin Fold Expansion |
|---|---|---|
| JK196P periportal Lnode | | |
| 5 | 1 | 1.7 |
| 7 | 4 | 10.2 |
| 11 | 15 | 82 |
| 15 | 16.2 | 114.8 |
| KM098 periportal Lnode | | |
| 4 | 1 | 1 |
| 6 | 1.6 | 6 |
| 8 | 2.9 | 36 |
| 11 | 12 | 130 |
| 13 | 20.6 | 223.6 |

Figure 8:
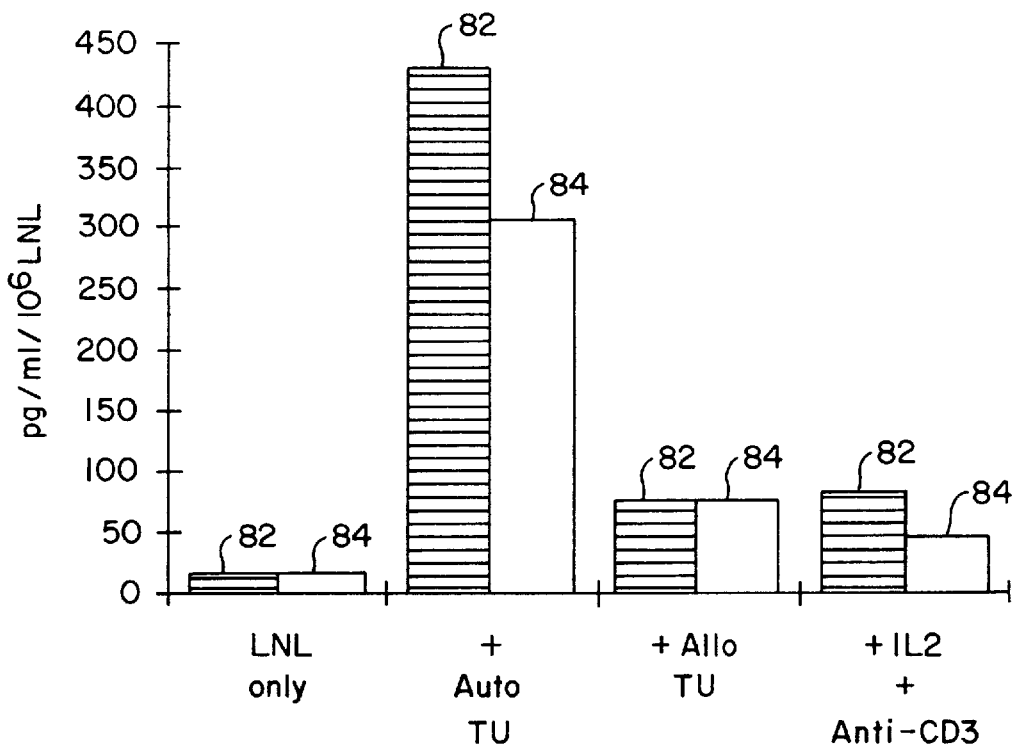
FIG. 8 graphically displays the production of tumor necrosis factor (TNF) alpha by expanded LNL cells cultured under two different sets of mitogenic stimulation conditions, or cultured in the presence of autologous tumor or allogeneic tumor.

Further characterization involved comparing tumor necrosis factor (TNF) alpha secretion by patient JG196 LNL's sample cultured alone and with either autologous tumor, allogeneic tumor, or anti-CD₃. The following results were recorded and are displayed in FIG. 8.

TABLE 11

| Patient JG 196 | TNF alpha (pg/ml/$10^6$ LNL) | |
|---|---|---|
| | IL-2 + anti-CD$_3$ cultured cells (item 82) | IL-2 + PMA + Ionomycin cultured cells (item 84) |
| LNL only | <15 | <15 |
| LNL + Autologous tumor | 428 | 305 |
| LNL + Allogeneic tumor | 75 | 75 |
| LNL + IL-2 + anti-CD$_3$ | 80 | 45 |

These results show that the LNL cells produce cytokine in the presence of autologous tumor. Further, expanded LNL cells produce cytokine in response to autologous tumor supporting that they are indeed tumor reactive lymphocytes.

EXAMPLE II

Later Experimental Procedures

Later experimental work conducted during the course of developing the present invention involved slight modifications to the procedures set forth above. Patient selection and surgery was substantially the same as described above with respect to the initial experimental procedures. Again, determination of the lymph nodes to be excised and used for cell expansion involved detecting the presence of the radiolabelled antibody with no macroscopic tumor evident (by visualization and palpation). This data was originally reported as follows: Triozzi, et al., Cancer, Vol. 73, No. 3, Feb. 1, 1994, the disclosure of which is expressly incorporated herein by reference.

Cells

Samples of lymph nodes and tumors not needed for diagnosis were obtained from resected specimens by a pathologist. Half of each lymph node was used for histopathology and the other half for immunologic studies. Dissociation of tissue was performed under sterile conditions in a laminar flow hood. Tissue was rinsed in a centrifuge tube with RPMI, antibiotic, and antimycotic (GIBCO, Grand Island, N.Y.) and was transferred to a Petri dish on ice. Extraneous tissue was excised with a scalpel, and the tissue was minced into pieces approximately 2–3 mm in diameter. Cells were separated by gentle dissociation with a blunt end of a 5-ml syringe and then washed twice with Hank's buffered saline solution. Cell viability was greater than 80% for all separations as assessed by the blue exclusion test. Peripheral blood lymphocytes were separated from study patients using standard gradient centrifugation techniques with Ficoll-Hypaque (Pharmacia, Piscataway, N.J.) of heparinized peripheral blood. All cells not needed immediately were cryopreserved in dimethyl sulfoxide with 5% autologous serum.

Fluorescence-Activated Cell Sorter Analysis

Cells, $10^6$ in 0.1 ml of culture media, were treated for one hour at 4° C. with 0.5 mg of the MoAb. After two washes, the secondary fluorescent goat antimouse IgG (Becton Dickinson, Mountain View, Calif.) at 1/40 dilution was added according to the recommendation of the manufacturer. The cells were labeled for one hour and after two washes analyzed by flow cytometry using a cytofluorograph. The following MoAb's were used: pan T-cell (Leu4; anti-CD$_3$), cytolytic/suppressor T-cell (Leu2a; anti-CD8), helper/inducer T-cell (Leu19; and anti-CD56) (all from Becton Dickinson); "naive" T-cell (2H4; anti-CD45RA) and "memory" T-cell (UCHL1; anti-CD45RO) (both from AMAC, Westbrook, Me.); and anti-HLA-DR (HB103; ATCC, Rockville, Md.).

Cytolytic Activity

Tumor cells were labeled with sodium chromate ($^{51}$Cr) using 100 $\mu$Ci/5×10$^6$ cells/0.5 ml for one hour at 37° C. Tumor cells ($10^4$/100 $\mu$l) were added to triplicate 6-mm round-bottomed plates. Natural killer-resistant Daudi cell targets were used as positive controls for the assays. Effector cells generated as described above were added in the same media (100 $\mu$l) to achieve effector-to-target ratios of 40:1, 20:1, 5:1, and 1.5:1. Also included were three maximum-release wells containing only labeled target cells plus Triton X-100 (Sigma Chemical Co., St. Louis, Mo.) and three spontaneous release wells. The plate was centrifuged (200×g for 5 minutes) and incubated at 37° C. for four hours. The plate was centrifuged again and 100 $\mu$l of supernatant was removed. The percentage of lysis was determined by the following formula: (experimental counts per minute [cpm] -spontaneous cpm)/(total cpm-spontaneous cpm). Each variable was tested in triplicate.

Proliferation Assay

Proliferation assays were performed by incubating $10^5$ lymphocytes, in both the presence and absence if IL-2, with BSM (Sigma Chemical Co., St. Louis, Mo.), which irradiated autologous and allogeneic tumor cells and with irradiated autologous normal colonic cells. After 96 hours in culture, cells were pulse-labeled with 1 mCi [$^3$H]thymidine for one hour at 37° C. and harvested using a cell harvester. Incorporated radioactivity was measured by scintillation counting.

Statistical Analysis

Paired and non-paired Student's t test and Mann-Whitney U test were used to determine the significance of differences between phenotypic and functional characteristics of the lymphocyte populations. Analysis of variance using regression models was used to assess differences in expansion rates.

Results

Lymph Nodes

Tissue was examined from 20 patients (8 women and 12 men) with recurrent and/or colorectal cancer taking part in the Phase I study. The mean age was 57 years (range, 33–72 years). From 1 to 11 (median 4) lymph nodes that appeared normal on inspection and palpation but that contained $^{125}$I-labeled CC49 were identified by the probe in these patients. Frequently these lymph nodes were characterized by very high levels of radioactivity (lymph node-to-background counts of greater than 10:1), and they were often identified in sites that classically have not been considered to be tumor-draining sites for colon carcinoma, such as the gastrohepatic, celiac, and iliac areas. Twenty-five clinically normal lymph nodes containing radiolabeled MoAb and six clinically normal lymph nodes (from five different study patients) that did not contain radiolabeled MoAb were excised for immunologic study.

The presence of tumor in the lymph nodes was evaluated using routine histologic evaluation, that is, hematoxylin and eosin (H and E) staining as well as immunohistochemistry using MoAb AE1-3 (Boehringer Mannheim, Indianapolis, Ind.) to identify cytokeratin. A modified avidin-biotin peroxidase complex technique (Vectastain, Vector, Burlingame, Calif.) was used to identify the murine MoAb. Usually, only one or two foci of tumor cells were found in lymph nodes localized by the probe on routine H and E staining; when tumor cells were not identified, immunohistochemical studies showed that CC49 distributed at germinal centers with a characteristic crescentic or circular dendritic pattern. The presence of tumor cells also was investigated by staining cytocentrifuge preparations prepared from the lymph nodes after dissociation and gradient centrifugation (Ficoll-Hypaque, Pharmacia).

The 25 clinically normal lymph nodes that contained radiolabeled MoAb were classified as containing either "microscopic tumor" or "shed antigen". Seventeen were classified as containing microscopic tumor, tumor cells were found after dissociation and gradient centrifugation of the lymph nodes in all 17; in 14 of these lymph nodes, tumor was also found on H and E staining of the half submitted to pathology. Tumor cells were not identified on dissociation nor on H and E in eight lymph nodes, and these were classified as containing shed antigen. Tumor was not identified on dissociation nor by H and E in the six clinically normal lymph nodes that did not contain radiolabeled MoAb.

Phenotype

The phenotype of lymphocytes from lymph nodes identified with the probe were compared with other lymphocyte populations (Table 9, below). Six different lymphocyte populations were studied: (1) lymph nodes with microscopic tumor, (2) lymph nodes with shed antigen, (3) lymph nodes with macroscopic tumor, (4) non-involved lymph nodes, (5) TIL; and (6) peripheral blood lymphocytes (PBL). Flow cytometry was performed to determine the phenotypic characteristics of the freshly isolated material. TIL were phenotyped after 24 hours in culture with 1000 U/ml IL-2 to improve separation and lymphocyte yields.

CD4-CD8 ratios from lymph nodes with microscopic tumor or shed antigen were greater than any other lymphocyte population ($P<0.05$). Lymph nodes identified by the probe and lymph nodes with macroscopic tumor had significantly more CD45RO+cells than did TIL, PBL, and non-involved lymph nodes ($P<0.05$). PBL had significantly more CD56+ cells than any of the populations and TIL ($P<0.001$). Phenotypic differences between lymph nodes with microscopic tumor and those with shed antigen were not detected.

split when confluent (every 3–6 days). Expansion of lymphocytes from lymph nodes with microscopic tumor and with shed antigen was comparable; both were significantly greater ($P<0.05$) than that of TIL, lymph nodes with macroscopic tumor, and non-involved lymph nodes. Expansion of lymphocytes from non-involved lymph nodes was significantly greater ($P<0.05$) than lymph nodes with macroscopic tumor and TIL. TIL populations usually developed into a combination of CD4+ and CD8+ or predominantly CD8+ populations. All lymph node lymphocyte populations developed into a combination of CD4+ and CD8+ with CD4+ populations predominating. It appeared that the emergence of CD8+ cells was associated with decrease in expansion in cultures and an increase in expansion in TIL cultures.

Proliferation

We first compared the proliferative responses of lymph nodes lymphocytes from lymph nodes identified by the Neoprobe® 1000 probe with lymph node lymphocytes from non-involved lymph nodes (from the same patient). Lymphocytes ($10^5$/well) were co-cultured for five days with irradiated (5000 R) autologous and allogeneic tumor cells (0–50,000/well) with and without 10 U/ml of IL-2. Lymphocytes also were exposed to a range of concentrations of BSM, which expresses CC49 binding epitopes, as a source of soluble TAG-72. [$^3$H]-thymidine was added 18 hours before harvest. Autologous tumor (50,000 cells) induced significant proliferation ([$^3$H]thymidine uptake in cpm more than three standard deviations of the unstimulated cells) in all lymph nodes identified with the probe (n=19 lymph nodes from 16 different patients), both in the presence and absence of IL-2. Autologous normal colonic cells and PBL did not induce proliferation in any study. The proliferative response of lymphocytes from lymph nodes with microscopic tumor was greater than that of lymphocytes from non-involved lymph nodes to autologous and to allogeneic TAG-72+ colorectal tumor specimens, both in the presence and absence of IL-2 ($P<0.01$). In contrast to lymphocytes from non-involved lymph nodes, lymphocytes from lymph nodes exposed to microscopic tumor proliferated in response to BSM in a dose-response manner. To characterize the

TABLE 12

Phenotype of Lymphocyte Populations*

|  | Microscopic Tumor (n = 12) | Shed Antigen (n = 8) | Macroscopic Tumor (n = 6) | Noninvolved (n = 6) | Tumor Lymphocyte (TIL) (n = 4) | Peripheral Blood Lymphocyte (PBL) (n = 9) |
| --- | --- | --- | --- | --- | --- | --- |
| CD3 | 73 ± 10 | 71 ± 15 | 64 ± 16 | 72 ± 20 | 72 ± 16 | 62 ± 13 |
| CD4 | 63 ± 11 | 59 ± 12 | 44 ± 15 | 50 ± 12 | 35 ± 6 | 41 ± 18 |
| CD8 | 10 ± 3 | 10 ± 4 | 19 ± 7 | 21 ± 11 | 24 ± 18 | 22 ± 4 |
| CD4/CD8 | 6.3 ± 0.9$^{ab}$ | 5.9 ± 1$^{ab}$ | 2.3 ± 0.8 | 2.4 ± 0.4 | 1.5 ± 0.5 | 1.9 ± 0.3 |
| CD56 | 4 ± 3 | 4 ± 3 | 1 ± 1 | 1 ± 1 | 1 ± 1 | 14 ± 5$^{ac}$ |
| CD45RA | 16 ± 8 | 17 ± 10 | 12 ± 10 | 33 ± 14$^{ad}$ | 18 ± 9 | 20 ± 14 |
| CD45RO | 40 ± 13$^{ae}$ | 38 ± 16$^{ae}$ | 37 ± 16$^{ae}$ | 20 ± 9 | 21 ± 12 | 29 ± 19 |
| HLA-DR | 31 ± 15 | 28 ± 6 | 27 ± 13 | 21 ± 15 | 24 ± 11 | 20 ± 15 |

*Lymphocytes from lymph nodes were analyzed using flow cytometry. Data obtained represent mean percentages of positive cells ± standard deviation.
[a]Significant differences.
[b]$P < 0.001$ versus macroscopic, noninvolved, TIL, and PBL.
[c]$P < 0.001$ versus microscopic, shed antigen, macroscopic, noninvolved, and TIL.
[d]$P < 0.01$ versus microscopic, shed antigen, macroscopic, TIL, and PBL.
[e]$P < 0.05$ versus TIL, PBL, and noninvolved.

Expansion

The expansion of the various lymphocyte populations in response to 1000 U/ml human recombinant IL-2 (recombinant human, Cetus, Emeryville, Calif.) also was examined. All cultures were stated at $10^6$ cells/ml and were possible role of CC49 as well as its binding epitope in the proliferative responses, lymph node lymphocytes from lymph nodes exposed to microscopic tumor were cultured in 10 U/ml of IL-2 for 4 days with no additions and in the presence of BSM (100 μg/ml), CC49 (0.1 μg/ml), and BSM plus CC49. CC49 alone did not enhance proliferation, and the combination of CC49 with BSM did not abrogate the proliferation induced by BSM alone.

Further examination of the proliferative responses of lymphocytes from lymph nodes identified by the probe were undertaken by comparing their proliferative responses to TAG-72$^+$ and to TAG-72$^-$ tumor cells. The following cells were evaluated: patient-derived autologous and allogeneic TAG-72$^+$ (i.e., CC49$^+$) colon cancer cells, including intensely TAG-72$^+$ cells from a patient with pseudomyxoma peritonaei; patient-derived TAG-72$^+$ breast cancer, patient derived TAG-72$^-$ squamous cell anorectal cancer, TAG-72$^-$ melanoma, and TAG-72$^-$ colorectal cancer, TAG-lymphoblastoid Daudi cells; and LS 174T cells (ATCC), a colon carcinoma cell line that expresses TAG-72 in vivo but not in vitro. Lymphocytes from lymph nodes with microscopic tumor proliferated to all TAG-72$^+$ tumor; proliferation of lymph nodes with microscopic tumor to patient-derived TAG$^+$ tumor cells was greater than that to TAG-72$^-$ cells (P=0.0001). These data are set forth below in Table 13.

TABLE 13

Proliferative Responses to Tumor Cells*

|  | No Mitogen | IL-2 |
| --- | --- | --- |
| No tumor cells | 444 ± 185 | 5476 ± 1800 |
| TAG-72$^+$ tumor cells |  |  |
| Autologous colon | 1428 ± 600 | 10,495 ± 1435 |
| Allogeneic colon | 1755 ± 531 | 9313 ± 1764 |
| Mucinous colon** | 5203 ± 1866 | 13,376 ± 2719 |
| Breast | 2571 ± 1519 | 10,302 ± 3277 |
| Tag-72$^-$ tumor cells |  |  |
| Colon | 884 ± 625 | 7621 ± 1319 |
| Rectal | 584 ± 268 | 7410 ± 152 |
| Daudi | 712 ± 217 | 8066 ± 3173 |
| LS174T | 124 ± 86 | 798 ± 282 |

*Lymphocytes from lymph nodes identified with the probe were stimulated with 50,000 irradiated tumor cells ± U/ml of IL-2 for four days. Data represent proliferate in CPM ± standard deviation for lymph nodes from four different patients. Differences in proliferation of lymphocytes to TAG-72$^+$ versus TAG-72$^-$ tumors were significant at P = 0.0001 in the presence and absence of mitogen.
**Mucinous colon: intensely TAG-72$^+$ cells from patient with *pseudomyxoma peritonea*.

Cultured LS174T cells inhibited the proliferative responses, suggesting the possibility of tumor-derived suppressive factors in this transformed cell line. The use of frozen LS174T cells as targets did not induce suppression.

Cytolytic Activity

In these experiments, dissociated lymph nodes and tumors as well as PBL populations were cultured with IL-2 at 1000 U/ml for up to 35 days. All cultures were started at 10$^6$ cells/ml and were split when confluent. Cytolytic activity of the lymphocytes that were expanded was evaluated in standard 4-hour $^{51}$Cr-release assays after 47 days and after 21–28 days of culture. Previously frozen autologous tumor, allogeneic tumor, and natural killer-resistant Daudi cells were used as targets. TAG-72- expressing tumor cells derived from one of two patients were used in all allogeneic assays; the cells from these two patients were equally sensitive (±10%) to lymphokine activated killer agents generated from healthy volunteers. These data are presented below in Table 14.

TABLE 14

Cytolytic Activity of Lymphocyte Populations$^a$

|  | Day | Microscopic Tumor (n = 7) | Shed Antigen (n = 6) | Macroscopic Tumor (n = 7) | Noninvolved (n = 6) | Tumor Lymphocyte (TIL) (n = 4) | Peripheral Blood Lymphocyte (PBL) (n = 7) |
| --- | --- | --- | --- | --- | --- | --- | --- |
| Autologous | 4–7 | 21 ± 8$^{bc}$ | 18 ± 6$^{bc}$ | 11 ± 6 | 9 ± 5 | 4 ± 4 | 39 ± 18$^{bd}$ |
|  | 21–28 | 2 ± 2 | 5 ± 3 | 3 ± 3 | 2 ± 1 | 6 ± 4 | 6 ± 4 |
| Allogeneic | 4–7 | 24 ± 8$^{bc}$ | 19 ± 6$^{bc}$ | 9 ± 4 | 8 ± 5 | 3 ± 4 | 51 ± 28$^{bd}$ |
|  | 21–28 | 3 ± 4 | 4 ± 3 | 2 ± 2 | 3 ± 2 | 4 ± 2 | 5 ± 4 |
| Daudi | 4–7 | 34 ± 14$^{bc}$ | 38 ± 11$^{bc}$ | 15 ± 7 | 10 ± 7 | 4 ± 2 | 73 ± 21$^{bd}$ |
|  | 21–28 | 4 ± 6 | 3 ± 3 | 3 ± 2 | 2 ± 3 | 5 ± 3 | 3 ± 2 |

$^a$Lymphocytes from lymph nodes were cultured with 1000 U/ml of IL-2, Cytolytic activity was determined versus patient-derived autologous and allogeneic TAG-72$^-$ tumor cells and versus TAG-72$^-$, natural killer-resistant, Daudi cells. Cytolytic activity was determined after 4 to 7 days of culture and after 21 to 28 days of culture. Data represent mean percentage lysis ± standard deviation at effector-to-target ratios of 40:1.
$^b$Significant difference.
$^c$P < 0.05 versus macroscopic, noninvolved, and TIL.
$^d$P < 0.001 versus microscopic and shed antigen and <0.0001 versus macroscopic, noninvolved, and TIL.

The highest level of cytolytic activity was generated from PBL. Cytolytic activity of lymph nodes with microscopic tumor and lymph nodes with shed antigen was comparable. Although less than cytolytic activity generated from PBL, cytolytic activity from these lymph nodes was consistently greater than that generated from TIL and from that generated from macroscopically involved and non-involved lymph nodes (P<0.05). Specific killing of autologous tumor was not observed at any time. Cytolytic activity decreased in all cultures with time.

Discussion

A technique has been developed by which tumor-reactive lymphocytes can be localized in vivo. By identifying lymph nodes with microscopic tumor and/or shed antigen, the use of radiolabeled MoAb in vivo and a gamma-detecting probe can reproducibly localize lymph node lymphocytes with reactivity against autologous tumor. Lymph nodes vary in their responsiveness to tumor. They are the initial site of metastasis in colorectal cancer and play an important role in host-tumor interactions. Many patients with colorectal cancer metastatic to lymph nodes have long-term survival with only a simple surgical procedure that encompasses the relevant draining lymph nodes. The present results support the existence of an immune response to microscopic tumor in the lymph nodes of patients with colorectal carcinoma, even in lymph nodes remote from the primary tumor. Our results confirm the poor immunologic responsiveness of lymphocytes associated with macroscopic tumor and of TIL.

When compared with lymphocytes from lymph nodes with microscopic tumor and shed antigen, lymphocytes from lymph nodes with macroscopic tumor, TIL, and non-involved lymph nodes appeared functionally depressed. Differences were evident in several studies of function, including cytolytic activity, proliferative responses, and expansion.

The contribution of the murine MoAb to the immunologic responses observed is not known. The immunohistologic features of the lymph nodes were located throughout the abdomen in patients with recurrent and/or metastatic disease using radiolabeled MoAb in vivo are similar to those reported in the immunohistologic studies of Mariani-Costantini, et al., "Immunohistochemical Evidence of Immune Response to Tumor-Associated Antigens in Lymph Nodes of Colon Carcinoma Patients", *Cancer*, 1991; 67:2880–66. These investigators applied (ex vivo) a variety of MoAb against TAG-72, including CC49, and MoAb against lymphocyte and monocyte/macrophage determinants to non-involved regional lymph node sections from patients with primary colorectal cancer. They also noted immunohistochemical reactions at germinal centers and concluded that the shed TAG-72 epitope was selectively recognized and presented to germinal center B-cells.

Other observations, in addition to the immunohistochemical studies of lymph nodes from patients who did not receive MoAb in vivo, suggest that MoAb CC49 was not central to the immunologic response. MoAb CC49 alone did not stimulate proliferation in vitro of lymph node lymphocytes identified by the probe. Lymph node lymphocytes reacting against autologous tumor were identified using the technique in patients in whom human antimurine MoAb antibody was detected and in patients in whom human antimurine MoAb antibody was not. Furthermore, the singular location of the lymph nodes as well as the fact that lymph nodes with macroscopic tumor and TIL also contained MoAb also speaks against the possibility that the immunologic changes observed were solely secondary to an antimurine MoAb response.

Lymph nodes identified with the probe were characterized by an increase in CD4:CD8 ratio. CD4+ cell pleocytosis is an important early event in inflammatory response. Lymphocyte phenotype of patients with cancer, including patients with colorectal cancer, has been extensively studied; the results from various study groups have not been consistent. Most investigations, including the current one, have found that the CD4:CD8 ratio of TEL is much lower than the 2:1 ratio usually observed in PBL and in non-involved lymph nodes. Other investigators also have observed increased CD4+ cells in lymph nodes of patients with colorectal cancer. Adachi, et al., reported significant increase of CD4+ cells in lymph nodes of patients with colorectal cancer. Adachi, et al., reported a significant increase of CD4+ cells in tumor free pericolic nodes compared with intermediate nodes (i.e., those of the arterial truncus) and compared with nodes from cholecystectomy procedures. Adachi, et al., "Immune Competent Cells of Regional Lymph Nodes in Colorectal Cancer Patients: I. Flow Cytometric Analysis of Lymphocyte Subpopulation", *J. Surg. Oncol.*, 1991; 46:110–6.

Lymph nodes identified with the probe consistently demonstrated proliferative responses to TAG-72+ tumor cells and to soluble mucin, suggesting prior sensitization. Although proliferative responses to TAG-72− tumor were less than those to TAG-72+ tumor, the specificity of proliferative responses and whether TAG-72/tumor-associated mucin were critical were not established. The addition of CC49 MoAb, which binds to a carbohydrate epitope, to the proliferation assays did not block the response.

Preferential killing of autologous tumor by any lymphocyte population was not observed. Rather, cytolytic activity against Daudi cells, allogeneic tumor, and autologous tumor occurred in parallel in all studies. The instant findings may be the consequence of the concentration of IL-2 used (1000 U/ml); most TIL cultured with IL-2 alone do not show major histocompatibility-restricted cytotoxicity, but instead show nonspecific cytotoxicity. Cytotoxic T-cells that recognize mucin appear to kill in a non-major histocompatibility-restricted fashion. It has been hypothesized that the polyvalent nature of mucin may allow for effective, simultaneous engagement of multiple T-cell receptors, thus obviating the need for major histocompatibility-restricted stabilization of the antigen-receptor complex. The results of the cytotoxicity and the proliferation studies would be consistent with non-major-histocompatibility-restricted interactions. Cytolytic activity of lymph nodes identified by the probe was greater than other lymph nodes but less than PBL. The results of previous studies of lymphocyte cytotoxicity have been at variance. Some studies have concluded that the nonspecific cytolytic activity of involved and non-involved lymph node lymphocytes and of TIL is lower than that of PBL. Others have reported that nonspecific killing generated from lymph nodes and TIL is comparable to or better than that of the corresponding PBL.

No differences were detected in lymphocyte phenotype and function between lymph nodes with microscopic tumor and those with shed antigen. Because regional lymph nodes in patients with colorectal cancer are potentially influenced by a variety of microbial and chemical antigents as a result of the tumor-induced breakdown of normal barriers, it has often been unclear whether immunologic changes observed in regional lymph nodes of colorectal cancers were the result of the tumor or of other bowel-derived secondary stimuli. The fact that immunologic changes were observed in lymph nodes remote from the primary tumor and remote from the colon itself suggests that the response was to the tumor and not to secondary bowel-derived stimuli.

EXAMPLE III

Further Experimental Procedures

Patient surgery, lymph node detection, and excision were conducted in the manner reported above. Analysis led to the following additional later experimental findings.

Cell Culture:

Lymphocyte suspensions were incubated under various conditions in 75 $cm^2$ tissue culture flasks (Falcon Co.) at an initial density of $10^6$ cells/ml in RPMI 1640 with 10% heat-inactivated human plasma, penicillin, and L-glutamine (GIBCO, Grand Island, N.Y.). Cultures were performed under sterile conditions at 37° C. in 5.0% $CO_2$ using a humidified tissue culture incubator (Forma Scientific). The cell cultures were split on day 4 to a density of $2.5 \times 10_5$ cells/ml, and on day 7 to a density of $5.0 \times 10_6$ by adding fresh media to the conditioned media. Cell numbers were determined by Coulter Counter and viability by blue exclusion. Cultures were performed using following biologic response modifiers: IL-1 (Immunex, Seattle Wash.), IL-2 (Cetus Corp., Emeryville, Calif.), IL-4 (Amgen, Thousand Oaks, Calif.), interferon-(IFN-γ) gamma (Biogen, Cambridge, Mass.), OKT3 anti-$CD_3$ antibody (Ortho, Raritan, N.J.), indomethacin, and cimetidine.

Phenotypic Analysis:

Lymphocyte phenotype was determined using monoclonal antibodies and FACS. Fresh LNLs and cultured lymphocytes were placed into V-shape 96-well plates (Linbro Co.) at $10_6$ cells into 50 μl. Hank's balanced salt solution (HBSS) with 10% FCS (FACS medium). Cells were incubated with murine monoclonal antibodies (Becton-Dickinson) at 0.2 μg in 20 μl at 4° C. for one hour. Microplates were centrifuged at 600 rpm and pellet vortexed and washed with 150 μl FACS media in triplicate. The cell pellets were vortexed and resuspended with 0.2 μg fluorescein-conjugated goat anti-mouse monoclonal antibody (Becton-Dickinson) at 4° C. for one hour. The FITC-stained cells were centrifuged and washed in FACS medium in triplicate and resuspended in 0.5 ml. FACS medium with 1% formalin and kept at 4° C. until analysis. Antibodies used were directed against the epitopes $CD_3$ (T-cell receptor), CD4 (T-helper/inducer), CD8 (T-cytotoxic/suppressor), CD25 (Tac/IL-2 receptor), CD45RA (naive), CD45RO (memory), CD56 (NK/LAK), CD19 (B-cell), CD14 (monocyte/macrophage), and fluorescein-conjugated goat anti-mouse IgG.

Lymphocyte Cytotoxicity:

Cytotoxicity of cultured lymphocytes was evaluated using standard 4 hr $^{51}$Cr release assay. Tumor cell targets of autologous colon cancer and NK-resistant Daudi cell lines were incubated with sodium chromate $^{51}$Cr 100 μCi/5×10$^6$ cells/0.5 ml. for one hour at 37° C. Cytotoxicity assay was carried out in 96 well microplates with $10^4$ tumor targets in 100 μl/well. Effector cells were added in 100 μl to attain effector:target (E:T) ratios of 1.5:1, 5:1, 20:1, and 40:1. Triton X-100 was added to labeled tumor targets for complete release; both complete release and spontaneous release samples were run as controls with each assay. The plates were incubated at 37° C. and 5% $CO_2$ for four hours before harvest. At the completion of the incubation period, 10 μl of supernatant without cells was carefully aspirated and counted. The percentage cytotoxicity was calculated by the formula: (experimental cpm-spontneous cpm)/(total cpm-spontaneous cpm).

Lymphoproliferative assay:

Proliferative response of lymphocytes was measured by $^3$H-thymidine incorporation. Lymphocytes were cultured in 96 well microtiter plates with $10^5$ cells/well in 0.2 ml complete media. Autologous tumor was digested with collagenase, washed, and irradiated with 3000 rad (Cesium source) before incubation with lymphocytes at a responder:stimulator ratio of 2:1. Lymphocytes were incubated for 96 hours and pulsed with 1.0 μCi/well $^3$H-thymidine (New England Nuclear) for the final 12 hours. Plates were harvested by Skatron Ph.D. (Cambridge Technology) onto nylon filters and counted in scintillation cocktail on a Beckman 6500 gamma counter.

IL-2 Production Assay:

IL-2 production of pre- and post-expansion lymphocytes was measured using IL-2-dependent CTLL cells. Briefly, after 1×10$_5$ lymphocytes were incubated in 96 well microplates overnight with biologic response modifiers, 10 μl of supernatant was aspirated from each well and transferred to a separate plate. CTLL cells were added to the plates at a density of 2×10$^3$ cells/well, and six hours later pulsed with 1 μCi/well of $^3$H-Thymidine. Plates were harvested at 12 hours and counted as described previously. The cpms of $^3$H-thymidine uptake of the CTLL to standard concentrations of IL-2 were run as positive controls.

Cytokine mRNA Analysis:

Cytokine mRNA was analyzed by reverse transcription and amplification using the polymerase chain reaction (PCR) as described by Morgan, et al., "Detection of Cytokine MnRNA in vivo by PCR: Problems and Solutions", *Transplantation*, 56;2: 437 (1993). Total RNA was extracted by homogenization in guanidine isothiocyanate buffer (4M guanidine isothiocyanate, 25 mM sodium citrate pH 7.0, 0.5% sodium sarkosyl, 0.7% β-mercaptoethanol) and ultracentrifugation over a 5.7M CsCl cushion. cDNA was prepared from 5 μg RNA using an oligo (dT) primer and 200 U MMLV reverse transcriptase. Samples were diluted with sterile water to a final volume of 150 μl for PCR. PCR amplification was performed using standard techniques in a Perkin-Elmer or Thermolyne Temptronic thermal cycler. cDNA (5 μl) was amplified in a 50 μl reaction containing 10 mM Tris-Cl, pH 8.3, 50 mM KCI, 1.5 mM $MgCl_2$, 0.2 mM dNTPs, 0.4 μM primers, and 1.25 U Taq polymerase. Cycle parameters 94° C., 1 min; 50° C. to 60° C., 2 min; 72° C., 1 min; 40 cycles. PCR products were analyzed by electrophoresis in 2% agarose gels and ethidium bromide staining. PCR primers for IL-2, IL-4, IL-5, tumor necrosis factor (TNF)-β, β-actin and interferon (IFN)-γ were from Brenner, et al., "Message Amplification Phenotyping: A Technique to Simultaneously Measure Multiple mRNAs from Small Numbers of Cells", *Biotechniques*, 7:1096 (1989), and were synthesized by Oligos, Etc. (Wilsonville, Oreg.).

Statistical Analysis:

Analysis of variance (ANOVA) was used to compare differences among treated groups in proliferation and IL-2 production assays; a nonparametric analysis was used to evaluate expansion indices.

Results

Expansion:

Lymph nodes from 30 patients undergoing surgery in accordance with the '840 patent were localized by CC49 monoclonal antibody and expanded ex vivo using a variety of biologic response modifiers. Expansion indices (i.e., fold-increase of total lymphocyte numbers) after short-term expansion (<21 days) are illustrated in Table 15.

TABLE 15

Expansion Indices of RIGS-Localized Lymph Nodes
LNLs were cultured at 1 × 10$^6$ cells/ml and split on days 4 and 10 for maximal proliferation. Data represent mean ± S.D. of expansion index (fold increase) of lymph node lymphocytes. Culture of RIGS-localized LNLs with IL-2/anti-$CD_3$ resulted in significantly higher fold increase as compared to I-2 and IL-1/IL-2 (p < 0.00001).

|  | Day 6 | Day 10 | Day 14 | Day 21 |
| --- | --- | --- | --- | --- |
| IL-2 1000 U | 0.94 ± 0.2 | 2.52 ± 0.8 | 7.84 ± 3.8 | 32.5 ± 12 |
| IL-1/IL-2 | 1.27 ± 0.3 | 3.6 ± 1.0 | 13.6 ± 8.2 | 41.3 ± 18 |
| IL-2/anti-$CD_3$ | 2.88 ± 1.8 | 36.0 ± 13 | 88.6 ± 21 | 173 ± 115 |

RIGS-localized LNL exhibited approximately 40-fold expansion in culture with IL-2 100 U/ml and IL-1 200 U/ml+IL-2 100 U/m. Lymph node populations incubated with I-2 100 U/ml and anti-$CD_3$ MAb showed significantly higher expansion than cultures with IL-2 alone (p<0.00001). The addition of IL-4 (100–1000 U/ml), interferony-γ (100–1000 U/ml), cimetidine (100 μg/ml), or indomethacin (100 μg/ml) to IL-2 containing cultures did not significantly alter expansion or phenotype at any time point.

Phenotype analysis was performed at various time periods to identify which populations of lymphocytes were growing in response to these culture conditions.

TABLE 16

Phenotype of Cultured Lymph Node Lymphocytes
Phenotype of RIGS-localized LNLs expanded with IL-2 1000 U/ml, IL-1 200 U/ml, and IL-2 100 U/ml., or IL-2 100 U/ml. and anti-$CD_3$ 0.1 g/ml. Results represent mean percentage ± SD of positively stained cells by FACS (n = 6 patients).

|  | CD4 | | CD8 | | CD10 | |
| --- | --- | --- | --- | --- | --- | --- |
|  | Day 0 | Day 10 | Day 0 | Day 10 | Day 0 | Day 10 |
| IL-2 | 74 ± 5.2 | 36 ± 2.4 | 14 ± 4 | 29 ± 12 | 7 ± 4 | 29 ± 5 |
| IL-1/IL-2 | 74 ± 5.2 | 44 ± 7.9 | 14 ± 4 | 33 ± 13 | 7 ± 4 | 23 ± 7 |
| IL-2/anti $CD_3$ | 74 ± 5.2 | 76 ± 10 | 14 ± 4 | 15 ± 10 | 7 ± 4 | 7.7 ± 5 |

Phenotype of fresh LNLs localized by RIGS at day 0 revealed at CD4/CD8 ratio of approximately 5:1. The CD4+ predominant phenotype was maintained in IL2/anti-$CD_3$ cells at day 10, whereas LNL cultured in IL-2 and IL-1/IL-2 resulted in a trend towards CD8+ and CD56+ phenotypes at day 10. Table 13 provides characterization of LNLs expanded in IL-2/anti-$CD_3$ from five patients.

TABLE 17

Phenotype of RIGS-Localized LNLs Cultured with IL-2/Anti-$CD_3$
Phenotype of RIGS-localized lymph nodes cultured in IL-2 100 U/ml. and anti-$CD_3$ antibody 0.1 μg/ml. at various time periods. Data represents the mean ± S.D. of percentage of positively stained cells (n = 5 patients).

|  | Day 4 | Day 7 | Day 10 | Day 14 | Day 21 |
| --- | --- | --- | --- | --- | --- |
| CD3 | 70 ± 16 | 85 ± 19 | 83 ± 18 | 89 ± 11 | 88 ± 13 |
| CD4 | 64 ± 17 | 74 ± 13 | 79 ± 21 | 78 ± 14 | 66 ± 12 |
| CD8 | 9 ± 5 | 16 ± 9 | 19 ± 4 | 23 ± 5 | 34 ± 9 |
| CD56 | 4 ± 3 | 6 ± 4 | 5 ± 4 | 3 ± 4 | 2 ± 2 |
| CD45RA | 13 ± 5 | 4 ± 6 | 13 ± 8 | 11 ± 9 | 13 ± 6 |
| CD45RO | 42 ± 11 | 74 ± 12 | 51 ± 13 | 78 ± 10 | 80 ± 8 |
| HLA-DR | 28 ± 7 | 64 ± 12 | 61 ± 11 | 83 ± 11 | 87 ± 5 |

Early in the culture period (<12 days), the CD4+ pleocytosis was maintained, and this correlated with an approximate 40-fold expansion by day 10. As the culture period extended beyond day 14, CD8+ cells were generated and the CD4:CD8 cell ratio decreased. An increase of CD45RO+ (memory) was observed throughout the culture period, as well as an increase in HLA-DR expression, suggestive of activation. Phenotypes associated with B-cells (CD 19) and monocytes (Leu-M3) were less than 5% of all cultures tested after day 10.

Cytotoxicity:

In order to evaluate whether these culture conditions resulted in the outgrowth of cytolytic lymphocytes, cytotoxicity was measured in vitro. Cytotoxicity against autologous colon tumor cells was observed before day 7, which subsequently diminished to insignificant levels after day 10 of culture. None of the culture conditions tested resulted in the long term outgrowth of cytolytic T-cells. Cytotoxicity against NK-resistant Daudi cells showed a similar kinetics over the culture period, suggesting that the cytotoxicity early in the culture period was related to lymphokine-activated killer cell (LAK) activity.

Proliferative Response of Expanded LNL:

In order to evaluate the ability of the expanded cells to proliferate, LNL cultured in IL-2/anti-$CD_3$ were tested in the presence of autologous tumor as well as bovine submaxillary mucin (BSM), which contains the CC49 epitope, at day 10. The following data were recorded.

TABLE 18

| Mitogen | Experiment 1 Response (cpm) | Experiment 2 Response (cpm) |
| --- | --- | --- |
| No Treatment | 777 ± 226 | 901 ± 223 |
| IL-2 | 17337 ± 3507 | 19283 ± 3199 |
| IL-2 + Tumor | 28527 ± 3969 | 30962 ± 4412 |
| IL-1 + BSM | 25585 ± 4941 | 30034 ± 1130 |

These results suggest that IL-2/anti-$CD_3$ expanded cells retain the ability to proliferate in response to soluble mucin as well as autologous tumor.

IL-2 Production:

In an attempt to evaluate the ability of the expanded cells to secrete cytokines, probe-localized LNL ('840 patent procedure) expanded in IL-2 and anti-$CD_3$ antibody were evaluated for IL-2 production on days 0 (pre-expansion) and 10 (post-expansion).

TABLE 19

IL-2 Production of IL-2/Anti-$CD_3$ Expanded LNLs
Expanded cells were incubated alone (NT) or with PMA 10 ng/ml. for 12 hours.
IL-2 production of supernatant was measured by CTLL $^3$H-thymidine incorporation over 12 hours. Results represent mean ± S.D. of quadruplicate determinations.
PMA-stimulated IL-2 production of Day 10 cultured lymphocytes was significantly higher as compared to Day 0 in all three experiments (p < 0.0001).

|  | Experiment 1 | | Experiment 2 | | Experiment 3 | |
| --- | --- | --- | --- | --- | --- | --- |
|  | NT | PMA | NT | PMA | NT | PMA |
| Day 0 | 1549 ± 123 | 4187 ± 416 | 1039 ± 145 | 3626 ± 1072 | 1522 ± 428 | 10648 ± 742 |
| Day 10 | 3776 ± 60 | 16919 ± 2136 | 1796 ± 472 | 15459 ± 739 | 4997 ± 258 | 21013 ± 1307 |

LNLs cultured for 10 days with IL-2 and anti-$CD_3$ retained the ability to secrete IL-2 in vitro. Although baseline values reflect patient variability, stimulation of expanded cells with Phorbol ester (PMA 10 ng/ml) consistently resulted in a significant increase in IL-2 production as compared to day 0 (p=0.0001).

Cytokine mRNA Expression:

Cytokine mRNA analysis of LNLs using RT-PCR was performed to confirm the potential of expanded effectors to product cytokines. Cytokine mRNA expression of day 10

Figure 9:
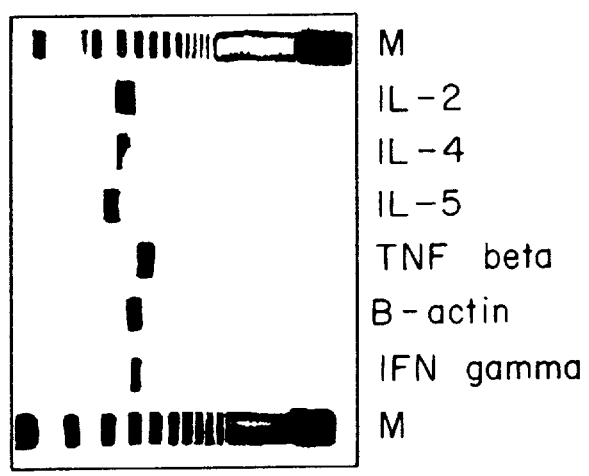
FIG. 9 displays cytokine mRNA expression of localized cells cultured in IL-2 (100 µg/ml) plus anti-$CD_3$ antibody (0.1 µg/ml) on day 10. Cytokine mRNA was analyzed by reverse transcription and cDNA amplified using the polymerase chain reaction (PCR). Lane M=123 bp molecular weight ladder (Gibco/BRL).
Figure 10:
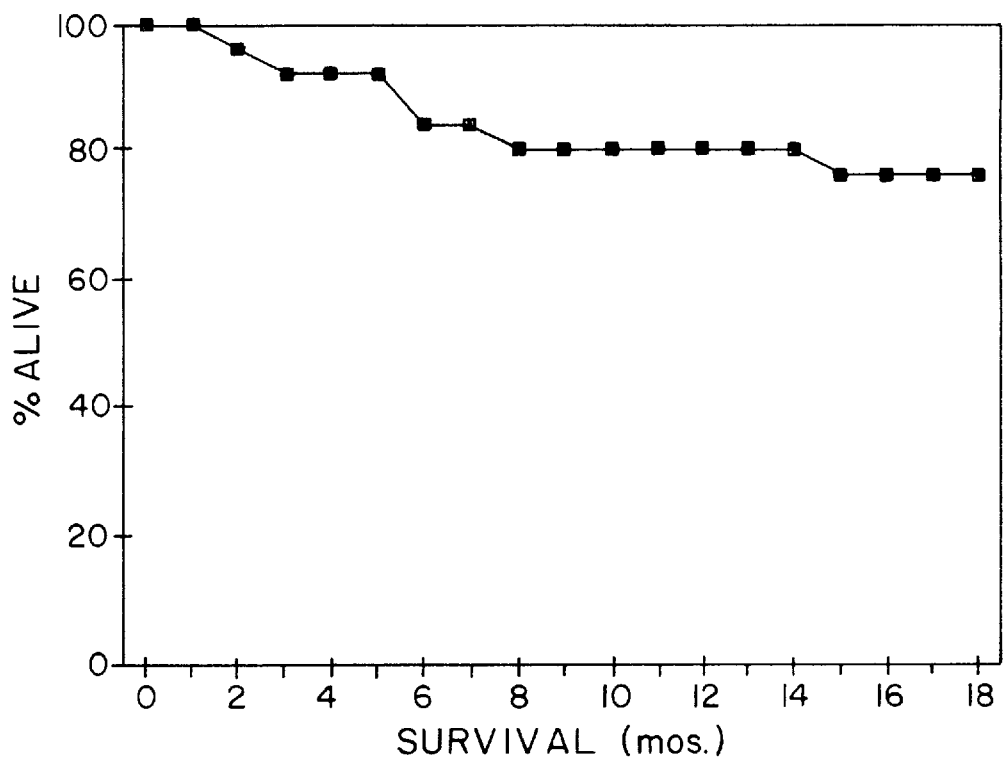
FIG. 10 graphically displays the percentage of patients alive after having received the novel therapeutic agent versus time (months) following administration of the agent.

LNLs expanded in IL-2/anti-CD$_3$ is shown at FIG. 9. This cultured cell population expressed a variety of mRNAs such as IL-2, IL-4, IL-5, IFNγ, and TNF-β, a pattern suggestive of a mixed Th1 and Th2 population.

Discussion:

Adoptive cellular therapy has demonstrated promise in clinical trials for some cancers, yet colorectal cancers, for the most part, have been resistant. Issues regarding the source of cells, methods of ex vivo activation, and mechanism of in vivo antitumor activity, are controversial. Although the characteristics of the optimal effector cells for adoptive cellular therapy have not been established, recent evidence suggests that in vivo effectiveness of adoptively transferred cells correlates better with the ability to secrete cytokines than with cytotoxicity in vitro. Barth, et al, "Interferon γ and tumor Necrosis Factor Have a Role in Tumor Regression Mediated by Murine CD8+ Tumor-Infiltrating Lymphocytes", *J. Exp. Med.*,173: 647 (1991). The present work includes the investigation of methods of expanding effectors from lymph nodes reacting against microscopic tumor and shed tumor mucin in vivo from patients with colorectal cancer using TAG-72-specific CC49 monoclonal antibody.

In an attempt to avoid suppression secondary to tumor-secreted factors, the '840 patent system was used to identify lymph nodes distant from the tumor that contained clinically occult, microscopic tumor and shed TAG-72. Data presented above demonstrates that the '840 patent localized lymph nodes are a good source of CD4+ cells that have undergone in vivo activation in response to micrometastatic tumor and shed tumor antigen. These localized lymph nodes are characterized by a CD4+ pleocytosis, a high percentage of which are CD45RO+ "memory" cells, in contrast to non-involved LNLs, which are predominantly CD45RA+ "naive". The in vitro proliferative response to mitogens of these LNLs with microscopic tumor and shed antigen is significantly higher and more specific than peripheral blood lymphocytes, TILs, non-involved lymph nodes, or nodes with macroscopic tumor.

Several lines of evidence are consistent with antigen-specific processing of TAG-72 antigen by these lymph nodes. Immunohistochemical studies by immunohistochemical staining in germinal centers of tumor-free lymph nodes of patients with colorectal cancer who have not previously received antibody; staining of these lymph nodes with anti-CEA antibodies failed to show the same pattern of antigen processing. In addition, in vitro proliferation of these lymph node lymphocytes to soluble TAG-72 mucin suggest that they have been sensitized to TAG-72 in vivo; similar responses to soluble CEA have not been seen.

The culture methods tested did not result in evidence of tumor-specific CTL generation, perhaps as a result of the limited culture interval as well as the conditions. Tumor mucin-specific (CTL) have been developed by Finn and coworkers by culturing tumor-draining lymph nodes of pancreatic cancer patients with IL-2 and repeated stimulation with tumor cells. Finn, Chapter on "Pancreatic Tumor Antigens: Diagnostic Markets and Targets for Immunotherapy", pp 61–77, found in DeVita, et al., *Important Advances in Oncology*, J. B. Lippincott, Philadelphia, Pa. (1992); and Jerome, et al., "Cytotoxic T-Lymphocytes Derived from Patients with Breast Adenocarcinoma Recognize an Epitope Present on the Protein Core of a Mucin Molecule Preferentially Expressed by Malignant Cells", *Cancer Res.*, 51:2908–2916, 1991; and Barnd, et al., *Proc. Natl. Acad. Sci. USA*, supra. These CTL, although mucin-specific, killed in a non-MHC-restricted fashion. Mariani-Constantini, et al., "Immunohistochemical Evidence of Immune Response to Tumor-Associated Antigens in Lymph Nodes of Colon Carcinoma Patients", *Cancer*, 67:2880 (1991). Because of predominance of CD4+ cells in cultures of '840 patent-localized lymph node lymphocytes, it is not surprising that direct cytotoxicity against tumor targets, in general, was low. Whether the LNLs detected by the '840 system are recognizing mucin core protein antigens in the non-MHC-restricted fashion as observed by Finn, et al., is under current investigation.

The adoptive transfer of noncytolytic, cytokine-secreting T-cells has been shown to promote the complete eradication of disseminated cancer in several animal models. Kahn, et al., "CD$_4$ Cell Clones Specific for the Human p97 Melanoma-Associated Antigen Can Eradicate Pulmonary Metastases from Murine Tumor Expressing the p97 Antigen", *J. Immunol.*, 146:3225 (1991); and Forni, et al., "Helper Strategy in tumor Immunology: Expansion of Helper Lymphocytes and Utilization of Helper Lymphokines for Experimental and Clinical Immunotherapy", *Can. Metast. Rev.*, 7:289 (1988). T-cells that secrete a number of cytokines have been shown to activate a variety of host effector mechanisms, including CTL, polymorphonuclear cells and tumoricidal macrophages. The presence of cytokine mRNA of IL-2, IL-4, TNF-β, and IFN-γ in IL-2/anti-CD$_3$ expanded cells suggests a mixed Th1 and Th2 phenotype that could include both cellular and humoral immune responses. The observation of significant IL-2 production by these '840 patent-localized LNLs following expansion suggests that they could function as T-helper cells in vivo. Control of tumor progression and regression has been observed in experimental animal models where low levels of IL-2 and IL-4 are continuously produced by gene-transfected tumor cells, presumably via recruitment of host effectors. Golumbek, et al., "Treatment of Established Renal Cancer by Tumor Cells Engineered to Secrete Interleukin-4", *Science*, 254:713 (1991).

The use of a radiolabeled monoclonal antibody to select LNL that are reacting against a specific tumor-associated mucin in vivo provides a unique opportunity for adoptive cellular immunotherapy of patients with advanced colorectal cancer. Since each '840 patent-localized lymph node contains approximately $5 \times 10^8$ cells, a 20-fold expansion will result in cell numbers, on a per-mass basis, effective in experimental animal models In order to demonstrate the tumor regression ability of the novel therapeutic agent disclosed herein, the following data is presented. This data is illustrative of the present invention and should not be construed as limiting.

EXAMPLE IV

Therapeutic Procedures

Colorectal Cancer Study

Twenty-seven patients have been enrolled in this colorectal cancer study. Each patient received $^{125}$I CC49 monoclonal antibody after which a delay interval elapsed as described above and taught in the '840 patent. Each patient then was subjected to surgery. Three patients were determined to be completely resectable and, therefore, were excluded from this study. The remaining 24 patients were determined to have disease which was not resectable. Lymph nodes were determined, however, and removed. Those lymph nodes determined by gross visual inspection to contain no tumor then were expanded in the manner described above. The patients were randomized to receive cells alone (no IL-2) the cells plus IL-2 administered to them. The following data were recorded:

TABLE 20

| Patient No. | Age/Sex | RIGS Date | Cells ($10^{10}$) | IL-2 | Best * Response | Comments |
|---|---|---|---|---|---|---|
| 1 | 54/M | 11/20/92 | 1.4 | – | SD | Chemotherapy began 4/93<br>Partial response noted 5/93 |
| 2 | 55/F | 12/10/92 | 4.0 | – | PD | Progressive disease; extensive tumor burden prior to therapy (hepatic mass 17 × 15 cm) |
| 3 | 37/F | 1/8/93 | 2.4 | – | CR | Tumor continues to regress--tumor was 5 × 5 cm; now <2 cm with extensive calcification (11/93) |
| 4 | 69/M | 1/29/93 | 3.3 | + | MR | >20% reduction in hepatic metastases after 1 month. Progression as of 4/28/93. Chemotherapy began 5/93 with a partial response |
| 5 | 37/M | 2/18/93 | 4.3 | + | SD | CA-125 decreased from 133 (4/93) to 62 (6/93). CEA is within normal limits (11/93) |
| 6 | 46/M | 3/5/93 | 7.3 | + | SD | Lung metastases as of 6/14/93 |
| 7 | 50/M | 3/26/93 | NA | NA | NA | Completely resected--off study |
| 8 | 70/M | 4/9/93 | 4.3 | + | SD | Progressed 9/8/93 |
| 9 | 54/M | 4/23/93 | 4.3 | + | PR | 6 cm × 6 cm lesion as cecum not seen (7/93) |
| 10 | 36/M | 6/18/93 | 3.2 | – | PD | 70% of liver replaced by tumor (progressed 8/25/93) |
| 11 | 70/F | 7/2/93 | 3.2 | + | SD | Progressed 10/6/93 |
| 12 | 23/M | 7/9/93 | 1.7 | + | PD | Expired 9/2/93 |
| 13 | 47/M | 7/23/93 | 0.6 | – | PD | Extensive tumor burden prior to therapy (11 cm × 12 cm liver lesion). New lesion 8/1/93. Expired 12/24/93 |
| 14 | 53/M | 7/30/93 | 0.4 | – | SD | Progressed 9/15/93 Stable from 9/15 to 11/17 |
| 15 | 58/F | 8/27/93 | NA | NA | NA | Completely resected--off study |
| 16 | 55/M | 9/3/93 | 2.3 | – | SD | Completed study |
| 17 | 68/F | 9/24/93 | 1.1 | – | SD | Completed study |
| 18 | 66/M | 10/8/93 | 5.4 | + | SD | Stable disease after 2 months |
| 19 | 65/M | 11/19/93 | 2.5 | + | SD | Stable disease after 2 months |
| 20 | 63/M | NA | NA | NA | NA | Completely resected--off study |
| 21 | 56/M | 2/25/94 | N/A | + | PD | Increase in all lesions. No new LFT's stable |
| 22 | 52/M | 3/11/94 | N/A | + | SD | |
| 23 | 59/F | 4/15/94 | 0.49 | – | N/A | |
| 24 | 46/M | 4/22/94 | 0.16 | – | N/A | |
| 25 | 50/M | 5/6/94 | N/A | – | N/A | |
| 26 | 64/F | 5/13/94 | N/A | – | N/A | |
| 27 | 59/M | 5/27/94 | N/A | – | N/A | |

* CR = complete response; PR = partial response; MR = minor response SD = stable disease; PD = progressive disease; NA = not applicable Clinical Responses. Two patients (Nos. 3 and 4) have shown evidence of tumor regression with and without exogenous IL-2. Follow-up scans assessing tumor response are pending for those patients still in the study.

Toxicity. Therapy was well-tolerated. There have been no complications related to cell infusions. All patients have reported fever and chill starting approximately 1 hour after cell infusion. These symptoms have been easily managed with medication. Asymptomatic and transient elevations of hepatic enzymes have been noted in patients receiving exogenous IL-2.

Immunologic Effects. Extensive immunologic data has been collected including surface phenotype, cytokine mRNA expression, and cytotoxicity of the expanded cells; DTH responses to autologous tumor (skin testing); peripheral blood cytotoxicity; peripheral blood cell phenotype; serum cytokines; and cell trafficking studies using $^{111}$In-labelled cells (patient 5). It is too early to draw any definitive conclusions.

The above data clearly demonstrate the efficacy of the therapeutic agent derived from the determined lymph nodes enriched in $CD_4$+ lymphocytes. Based on the response noted in patient 4, subjecting the patients that have received the therapeutic agent of this invention to adjuvant chemotherapy may be of particular benefit to the patient; even to those patients that were recalcitrant to chemotherapy prior to receiving the inventive adoptive cellular therapy treatment disclosed herein. This is particularly important in view of the National Institutes of Health (NIH) consensus report concerning the administration of adjuvant chemotherapy to appropriately staged patients. "NIH Consensus Conference: Adjuvant Therapy for Patients with Colon and Rectal Cancer", *JAMA*, 1990; 264:1444–50.

Buroker, et al, "Randomized Comparison of Two Schedules of Fluorouracil and Leucovorin in the Treatment of Advanced Colorectal Cancer", *J. Clin. Oncol*, Vol. 12, No. 1, pp 14–20 (January 1994), report survival of 372 patients receiving two different regimens of 5FU/Leucovarin of 9.3 and 10.7 months (median); while Stangl, et al., "Factors Influencing the Natural History of Colorectal Liver Metastases", *Lancet*, 1994; 343:1405–10, report that in 484 untreated patients, median survival was 7.5 months from the time of diagnosis; while for patients who underwent regional or systemic chemotherapy, median survival times were 12.7 and 11.1 months, respectively. FIG. 12 graphically displays the number of patients (see Table 20) that are alive following administration of the novel therapeutic agent versus time following such administration. Though these results are preliminary and for a small patient population, patient benefit appears to be seen.

Pancreatic Cancer Study

Two patients have been enrolled in this pancreatic cancer study thus far. Each patient received $^{125}$I CC49 monoclonal antibody after which a delay interval elapsed as described above and taught in the '840 patent. Each patient then was subjected to surgery. These 2 patients were determined to have disease which was not resectable. Lymph nodes were determined, however, and removed. Those lymph nodes determined by gross visual inspection to contain no tumor then were expanded in the manner described above. The patients were randomized to receive cells alone (no IL-2) the cells plus IL-2 administered to them. The following data were recorded:

TABLE 21

| Patient No. | Age/Sex | RIGS Date | Cells ($10^{10}$) | IL-2 | Best * Response | Comments |
|---|---|---|---|---|---|---|
| 1 | 62/F | 4/1/94 | N/A | – | PD | |
| 2 | 69/F | 4/1/94 | N/A | + | N/A | |

* CR = complete response; PR = partial response; MR = minor response SD = stable disease; PD = progressive disease; NA = not applicable

We claim:

1. A method for determining lymph nodes enriched in tumor-specific lymphocytes comprising $CD_4+$ tumor-specific lymphocytes from those lymph nodes not so enriched, which comprises the steps of:
   (a) administering to a human patient an effective amount of a photon-emitting radiolabelled locator which specifically binds a marker produced by or associated with neoplastic tissue;
   (b) permitting time to elapse following step (a) for said radiolabelled locator to preferentially concentrate in any neoplastic tissue and for unbound radiolabelled locator to be cleared so as to increase the ratio of photon emissions from neoplastic tissue to background photon emissions in said patient;
   (c) after said time has elapsed in step (b), accessing said patient with a radiation detection probe for determining lymph node sites exhibiting accretion of said radiolabelled locator by detecting with said probe elevated levels of radiation at said lymph node sites;
   (d) removing lymph nodes at said sites determined in step (c);
   (e) selecting those removed lymph nodes which visually do not contain evidence of tumor, wherein said selected lymph nodes are enriched in at least About 40% CD4+ tumor-specific lymphocytes; and
   (f) culturing said lymph nodes selected in step (e) to proliferate tumor-specific lymphocytes therein.

2. The method of claim 1, wherein the removed lymph nodes removed in step (d) are those that evidence no macroscopic tumor by visualization and palpation.

3. The method of claim 1, wherein said selected lymph nodes are cultured in step (f) by mitogenic stimulation.

4. The method of claim 3, wherein said lymph nodes in step (f) are cultured in the presence of Interleukin-2 and anti-CD3 monoclonal antibody.

5. The method of claim 4, wherein said culturing further includes a tumor-associated glycoprotein (TAG) antigen.

6. The method of claim 4, wherein said culturing further includes neoplastic tissue comprising one or more of autologous neoplastic tissue or allogeneic neoplastic tissue.

7. The method of claim 4, wherein the amount of Interleukin-2 ranges from between about 10 and 500 μg/ml and the amount of anti-CD3 monoclonal antibody ranges from between about 10 and 500 ng/ml.

8. The method of claim 6, which includes the step of inactivating said neoplastic tissue prior to said culturing step (g).

9. The method of claim 8, wherein said inactivating step includes irradiating said neoplastic tissue with a source of radiation for its inactivation.

10. The method of claim 1, which includes the step of separating said $CD_4+$ lymphocytes from said lymph nodes selected in step (e) for culturing in step (f).

11. The method of claim 1, wherein said lymphocytes cultured in step (f) are derived from splenic lymphocytes.

12. The method of claim 1 wherein said locator is one or more of a polyclonal antibody, monoclonal antibody, antibody fragment, a single chain antibody thereof, or a hormone.

13. The method of claim 1 wherein said locator is selected from $A_5B_7$ monoclonal antibody, CC49 monoclonal antibody, CC83 antibody, and combinations thereof.

14. The method of claim 1 wherein said radiolabelled locator emits gamma radiation or beta radiation and said method includes the step of detecting said gamma or beta radiation by said radiation detection probe.

15. The method of claim 14 wherein said radiolabelled locator exhibits select energy levels of not above about 550 kev.

16. The method of claim 15 wherein said radiolabel of said radiolabelled locator comprises $^{125}$I.

17. The method of claim 1 wherein said radiolabel of said radiolabelled locator comprises $^{125}$I.

18. The method of claim 4 wherein said radiolabel of said radiolabelled locator comprises $^{125}$I.

19. The methods of claim 1 wherin said patient is surgically accessed in step (c) with a manually-positionable portable radiation detection probe.

20. The method of claim 1, wherein said accessing step (c) further includes accessing said patient with an endoscope or laproscope.

21. The method of claim 1, which includes the step of coupling said radiation detection probe to a sound generator responsive to the presence of said elevated levels of radiation.

22. The method of claim 1, wherein said ratio in step (b) is greater than 1.5:1.

23. The method of claim 4, wherein said accessing step (c) further includes accessing said patient with an endoscope or laparoscope.

24. The method of claim 1, which includes the step of administering to said patient said cultured lymph nodes of step (f).

25. The method of claim 7, which includes the step of administering to said patient said cultured lymph nodes of step (f).

26. The method of claim 9, which includes the step of administering to said patient said cultured lymph nodes of step (f).

27. A method for effecting tumor regression in a human patient having tumors, which comprises administering to said patient an effective amount of the therapeutic agent which comprises a pharmaceutically-acceptable carrier and lymphocyte cells in an amount effective for tumor regression, wherein said lymphocyte cells have been produced by the step of mitogenically stimulating human patient excised lymph nodes enriched in tumor-specific lymphocytes comprising CD4+ tumor-specific lypmhocytes.

28. A method for effecting tumor regression in a human patient having tumors, which comprises administering to said patient an effective amount of the therapeutic agent which comprises a pharmaceutically-acceptable carrier and lymphocyte cells in an amount effective for tumor regression, wherein said lymphocyte cells have been produced by the step of mitogenically stimulating human patient excised lymph nodes enriched in tumor-specific lymphocytes comprising CD4+ tumor-specific lymphocytes, wherein the mitogenic stimulation of said lymph nodes comprises their culturing in the presence of Interleukin-2 and anti-CD3 monoclonal antibody.

29. A method for effecting tumor regression in a human patient having tumors, which comprises administering to said patient an effective amount of the therapeutic agent which comprises a pharmaceutically-acceptable carrier and lymphocyte cells in an amount effective for tumor regression, wherein said lymphocyte cells have been produced by the step of mitogenically stimulating human patient excised lymph nodes enriched in tumor-specific lymphocytes comprising -CD4+ tumor-specific lymphocytes, wherein the mitogenic stimulation of said lymph nodes comprises their culturing in the presence of Interleukin-2, anti-CD3 monoclonal antibody, and one or more of a tumor-associated glycoprotein (TAG) antigen or neoplastic tissue.

30. A method for effecting tumor regression in a human patient having tumors, which comprises administering to said patient an effective amount of the therapeutic agent which comprises a pharmaceutically-acceptable carrier and lymphocyte cells in an amount effective for tumor regression, wherein said lymphocyte cells have been produced by the step of mitogenically stimulating human patient excised lymph nodes enriched in tumor-specific lymphocytes comprising CD4+ tumor-specific lymphocytes, wherein the mitogenic stimulation of said lymph nodes comprises their culturing in the presence of Interleukin-2, anti-CD3 monoclonal antibody, and autologous or allogeneic neoplastic tissue which neoplastic tissue has been inactivated by irradiation with a source of radiation prior to its culturing with said lymph nodes.

31. A method for effecting tumor regression in a human patient having tumors, which comprises administering to said patient an effective amount of the therapeutic agent which comprises a pharmaceutically-acceptable carrier and human patient splenic lymphocytes in an amount effective for tumor regression, wherein said splenic lymphocytes have been produced by the step of mitogenically simulating patient excised splenic lymphocytes enriched in tumor-specific lymphocytes comprising CD4+ tumor-specific lymphocytes.

32. The method of claim 27, wherein said human patient is thereafter subjected to adjuvent chemotherapy.

33. A method for culturing human patient excised lymph nodes enriched in tumor-specific lymphocytes comprising $CD_4$+ tumor-specific lymphocytes, which comprises the steps of:
   (a) separating lymph node lymphocytes (LNL) from said excised lymph nodes;
   (b) culturing said LNL under mitogenic stimulation conditions to expand said LNL; and
   (c) thereafter, diminishing said mitogenic stimulation.

34. The method of claim 33, wherein said LNL are cultured in the presence of Interleukin-2 (IL-2), anti-CD3 monoclonal antibody, and a tumor-associated glycoprotein (TAG) antigen.

35. The method of claim 34, wherein the amount of Interleukin-2 ranges from between about 10 and 500 µg/ml and the amount of anti-CD3 monoclonal antibody ranges from between about 10 and 500 ng/ml.

36. The method of claim 34, wherein said IL-2 and said anti-CD3, which is soluble, are simultaneously added to said LNL.

37. The method of claim 33, wherein said LNL are cultured in serum-free media.

38. A method for culturing human patient excised lymph nodes enriched in tumor reactive cells, which comprises the steps of:
   (a) separating tumor reactive cells from said excised lymph nodes;
   (b) culturing said tumor reactive cells under mitogenic stimulation conditions to expand said tumor reactive cells; and
   (c) thereafter, diminishing said mitogenic stimulation.

39. The method of claim 33, wherein said tumor reactive cells are cultured in the presence of Interleukin-2 (IL-2), anti-CD3 monoclonal antibody, and a tumor-associated glycoprotein (TAG) antigen.

40. The method of claim 39, wherein the amount of Interleukin-2 ranges from between about 10 and 500 µg/ml and the amount of anti-CD3 monoclonal antibody ranges from between about 10 and 500 ng/ml.

41. The method of claim 39, wherein said IL-2 and said anti-CD3, which is soluble, are simultaneously added to said tumor reactive cells.

42. The method of claim 38, wherein said tumor reactive cells are cultured in serum-free media.

43. A method for mitigating tumor progression in a human patient having tumor, which comprises administering to said human patient an effective amount of the therapeutic agent which comprises a pharmaceutically-acceptable carrier and lymphocyte cells in an amount effective for mitigating tumor progression, wherein said lymphocyte cells have been produced by the step of mitogenically stimulating human patient excised lymph nodes enriched in tumor reactive cells.

44. A method for mitigating tumor progression in a human patient having tumor, which comprises administering to said patient an effective amount of the therapeutic agent which comprises a pharmaceutically-acceptable carrier and lymphocyte cell in an amount effective for mitigating tumor progression, wherein said lymphocyte cells have been produced by the step of mitogenically stimulating human patient excised lymph nodes enriched in tumor reactive cells, wherein the mitogenic stimulation of said lymph nodes comprises their culturing in the presence of Interleukin-2 and anti-CD3 monoclonal antibody.

45. A method for mitigating tumor progression in a human patient having tumor, which comprises administering to said patient an effective amount of the therapeutic agent of which comprises a pharmaceutically-acceptable carrier and lymphocyte cells in amount effective for mitigating tumor progression, wherein said lymphocyte cells have been produced by the step of mitogenically stimulating human patient excised lymph nodes enriched in tumor reactive cells, wherein the mitogenic stimulation of said lymph nodes comprises their culturing in the presence of Interleukin-2, anti-CD3 monoclonal antibody, and one or more of a tumor-associated glycoprotein (TAG) antigen or neoplastic tissue.

46. A method for mitigating tumor progression in a human patient having tumor, which comprises administering to said patient an effective amount of the therapeutic agent which comprises a pharmaceutically-acceptable carrier and lymphocyte cells in an amount effective for mitigating tumor progression, wherein said lymphocyte cells have been produced by the step of mitogenically simulating human patient excised lymph nodes enriched in tumor reactive cells, wherein the mitogenic stimulation of said lymph nodes comprises their culturing in the presence of Interleukin-2, anti-CD3 monoclonal antibody, and inactivated by irradiation with a source of radiation autologous or allogeneic neoplastic tissue.

47. A method for mitigating tumor progression in a human patient having tumor, which comprises administering to said patient an effective amount of the therapeutic agent of which comprises a pharmaceutically-acceptable carrier and human patient splenic lymphocyte in an amount effective for tumor regression, wherein said splenic lymphocytes have been produced by the step of mitogenically stimulating patient excised splenic lymphocyte enriched in tumor-specific lymphocytes comprising CD4+ tumor-specific lymphocytes.

48. The method of claim 43, wherein said patient is thereafter subjected to adjuvent chemotherapy.

* * * * *